(12) United States Patent
Zergiebel et al.

(10) Patent No.: US 12,156,652 B2
(45) Date of Patent: Dec. 3, 2024

(54) ADAPTER ASSEMBLY FOR INTERCONNECTING ELECTROMECHANICAL SURGICAL DEVICES AND SURGICAL LOADING UNITS, AND SURGICAL SYSTEMS THEREOF

(71) Applicant: Covidien LP, Mansfield, MA (US)

(72) Inventors: Earl M. Zergiebel, Guilford, CT (US); David M. Chowaniec, Rocky Hill, CT (US); Ryan Williams, New Hartford, CT (US); Anand Subramanian, Stamford, CT (US)

(73) Assignee: Covidien LP, Mansfield, MA (US)

( * ) Notice: Subject to any disclaimer, the term of this patent is extended or adjusted under 35 U.S.C. 154(b) by 255 days.

(21) Appl. No.: 17/679,171

(22) Filed: Feb. 24, 2022

(65) Prior Publication Data

US 2022/0175376 A1  Jun. 9, 2022

Related U.S. Application Data

(63) Continuation of application No. 16/774,375, filed on Jan. 28, 2020, now Pat. No. 11,266,404, which is a continuation of application No. 16/139,839, filed on Sep. 24, 2018, now Pat. No. 10,548,596, which is a continuation of application No. 15/708,520, filed on
(Continued)

(51) Int. Cl.
| | |
|---|---|
| *A61B 17/072* | (2006.01) |
| *A61B 17/068* | (2006.01) |
| *H01R 13/405* | (2006.01) |
| *A61B 17/00* | (2006.01) |

(52) U.S. Cl.
CPC .......... *A61B 17/072* (2013.01); *A61B 17/068* (2013.01); *A61B 17/07207* (2013.01); *H01R 13/405* (2013.01); *A61B 2017/00017* (2013.01); *A61B 2017/00398* (2013.01); *A61B 2017/0046* (2013.01); *A61B 2017/00464* (2013.01); *A61B 2017/00473* (2013.01);
(Continued)

(58) Field of Classification Search
CPC ........................................................ A24F 47/00
USPC ................................................. 131/328–329
See application file for complete search history.

(56) References Cited

U.S. PATENT DOCUMENTS

| | | | |
|---|---|---|---|
| 2,777,340 | A | 1/1957 | Hettwer et al. |
| 2,957,353 | A | 10/1960 | Babacz |

(Continued)

FOREIGN PATENT DOCUMENTS

| | | |
|---|---|---|
| AU | 2008229795 A1 | 4/2009 |
| CA | 2451558 A1 | 1/2003 |

(Continued)

OTHER PUBLICATIONS

European Search Report corresponding to EP 15 17 3807.7 dated Nov. 24, 2015.
(Continued)

*Primary Examiner* — Phuong K Dinh

(57) ABSTRACT

The present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

17 Claims, 28 Drawing Sheets

Related U.S. Application Data

Sep. 19, 2017, now Pat. No. 10,098,637, which is a continuation of application No. 14/700,917, filed on Apr. 30, 2015, now Pat. No. 9,763,661.

(60) Provisional application No. 62/017,510, filed on Jun. 26, 2014.

(52) U.S. Cl.
CPC .............. *A61B 2017/00477* (2013.01); *A61B 2017/07271* (2013.01); *A61B 2017/07285* (2013.01)

(56) References Cited

U.S. PATENT DOCUMENTS

| | | |
|---|---|---|
| 3,111,328 A | 11/1963 | Rito et al. |
| 3,388,590 A * | 6/1968 | Dryden .............. H01R 13/6683 73/862.541 |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,790,776 A * | 12/1988 | Iijima .................... H01R 24/28 439/736 |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,231,358 B1 * | 5/2001 | Kerr, Jr. ................. H01R 24/66 439/140 |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,896 B2 * | 1/2006 | Su .......................... H01R 43/24 439/693 |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,125,286 B2 | 10/2006 | Wang et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |

(56) References Cited

U.S. PATENT DOCUMENTS

| | | | |
|---|---|---|---|
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,177,782 B2 * | 5/2012 | Beller ............... A61B 18/1233 606/34 |
| 8,182,494 B1 | 5/2012 | Yencho et al. |
| 8,186,555 B2 | 5/2012 | Shelton, Iv et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |

(56) References Cited

U.S. PATENT DOCUMENTS

| | | |
|---|---|---|
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,597,104 B2 | 3/2017 | Nicholas et al. |
| 9,763,661 B2 | 9/2017 | Zergiebel et al. |
| 9,868,198 B2 | 1/2018 | Nicholas et al. |
| 10,098,637 B2 | 10/2018 | Zergiebel |
| 10,548,596 B2 | 2/2020 | Zergiebel et al. |
| 10,588,629 B2 | 3/2020 | Malinouskas et al. |
| 11,266,404 B2 | 3/2022 | Zergiebel et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton, IV et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0076865 A1 | 3/2011 | Luo et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Lizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0039302 A1 | 2/2014 | Miller et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |

(56) References Cited

U.S. PATENT DOCUMENTS

| | | |
|---|---|---|
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A2 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2668913 A2 | 12/2013 |
| EP | 2676615 A2 | 12/2013 |
| EP | 2881046 A2 | 6/2015 |
| ES | 2333509 A1 | 2/2010 |
| JP | 08038488 | 2/1996 |
| JP | 2005125075 A | 5/2005 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A3 | 4/2004 |
| WO | 2004107989 A1 | 12/2004 |
| WO | 2006042210 A2 | 4/2006 |
| WO | 2007014355 A2 | 2/2007 |
| WO | 2007016290 A2 | 2/2007 |
| WO | 2007026354 A1 | 3/2007 |
| WO | 2007137304 A2 | 11/2007 |
| WO | 2008131362 A2 | 10/2008 |
| WO | 2008133956 A2 | 11/2008 |
| WO | 2009039506 A1 | 3/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012040984 A1 | 4/2012 |

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.

(56) References Cited

OTHER PUBLICATIONS

Extended European Search Report corresponding to International Application No. EP 15 18 4915.5 dated Jan. 5, 2016.
European Office Action corresponding to counterpart Patent Appln. EP 15173807.7 dated Jan. 3, 2019.
Chinese First Office Action corresponding to counterpart Patent Appln. CN 201510363069.5 dated Jul. 31, 2018.
Australian Examination Report No. 1 dated Oct. 29, 2020 corresponding to counterpart Patent Application AU 2020217315.

* cited by examiner

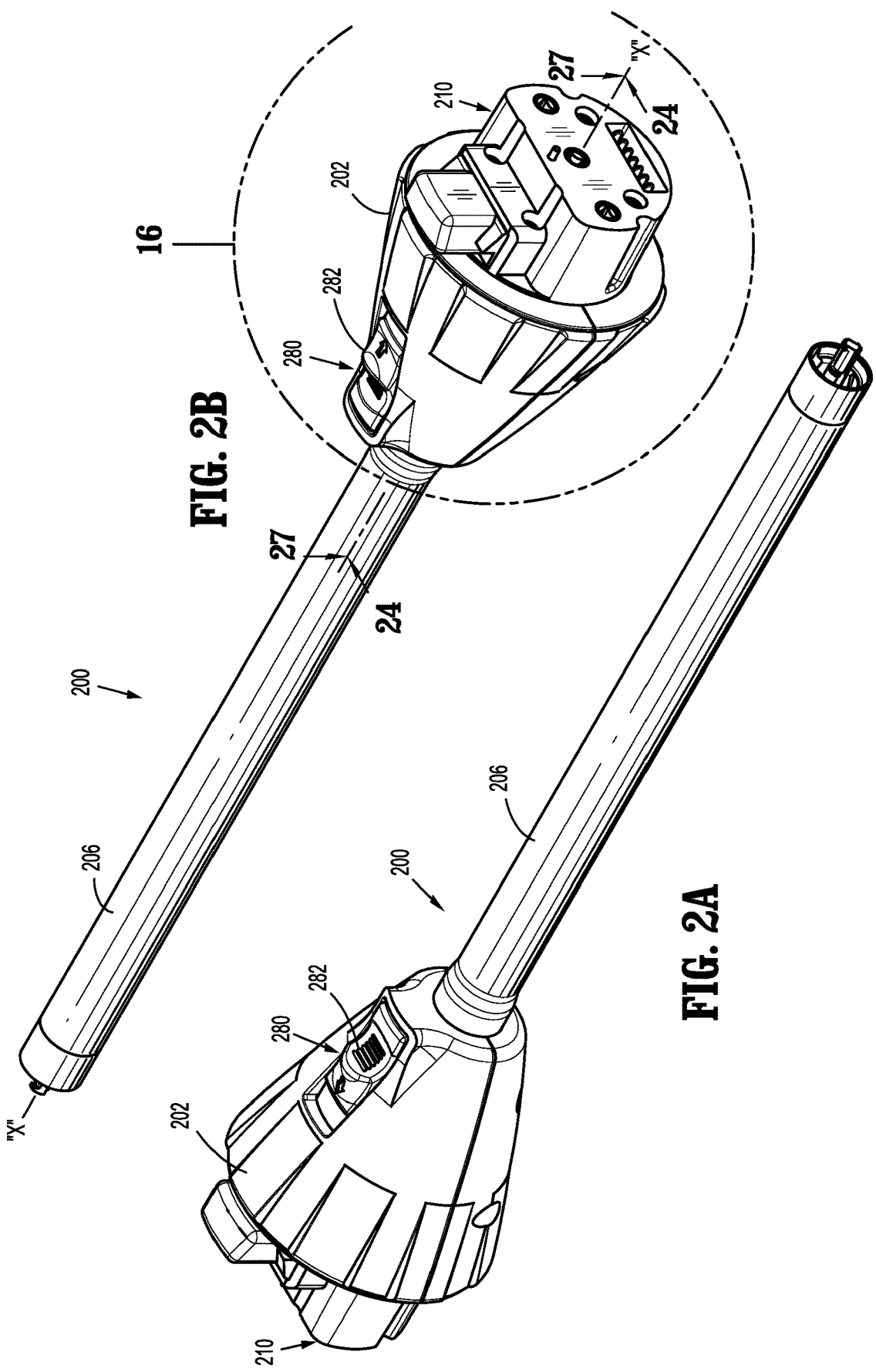

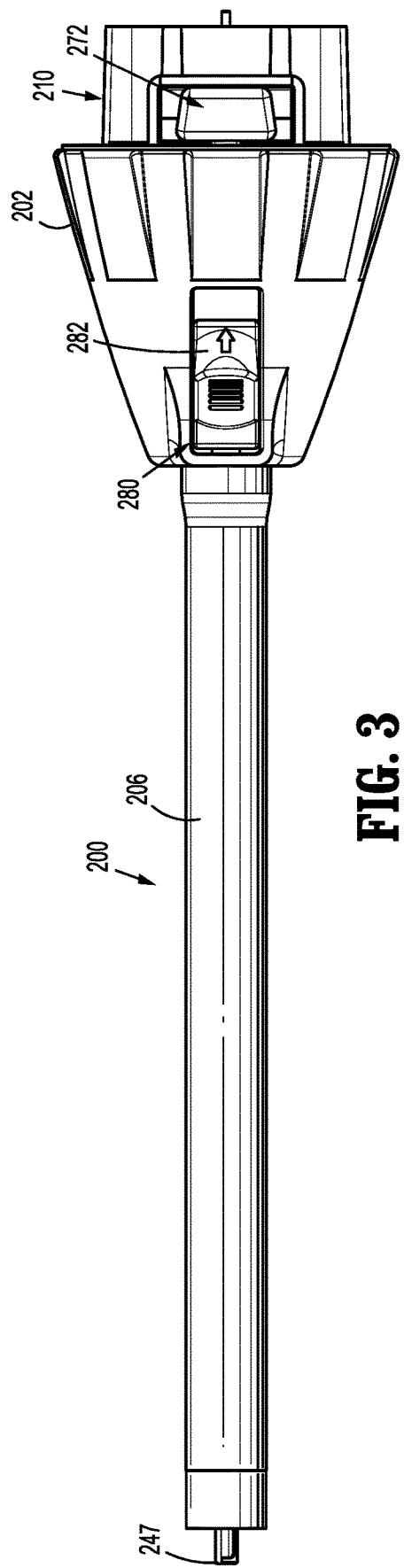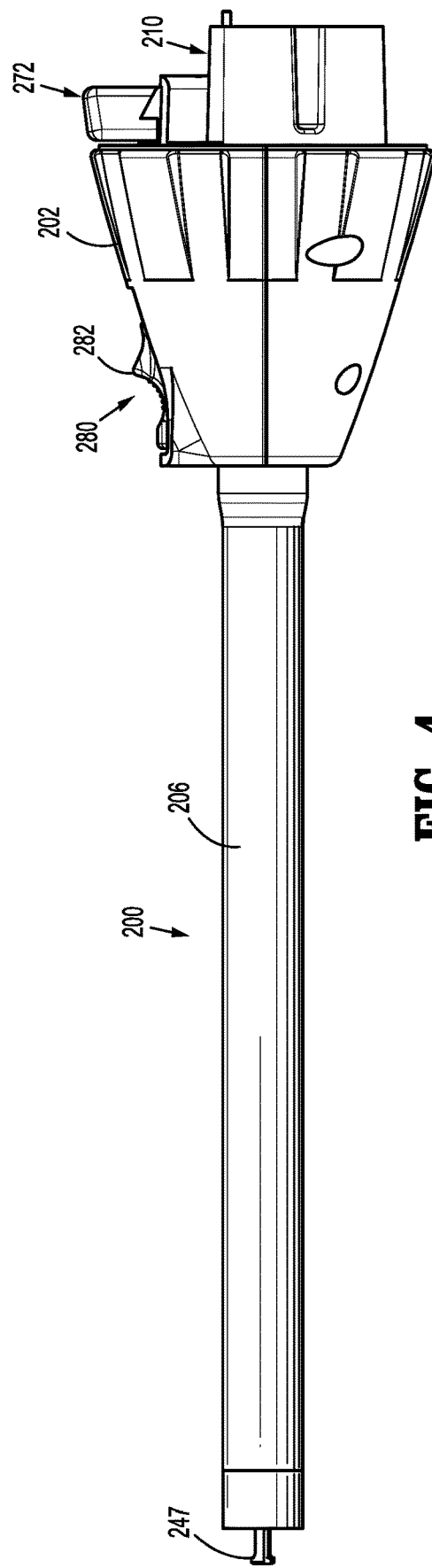

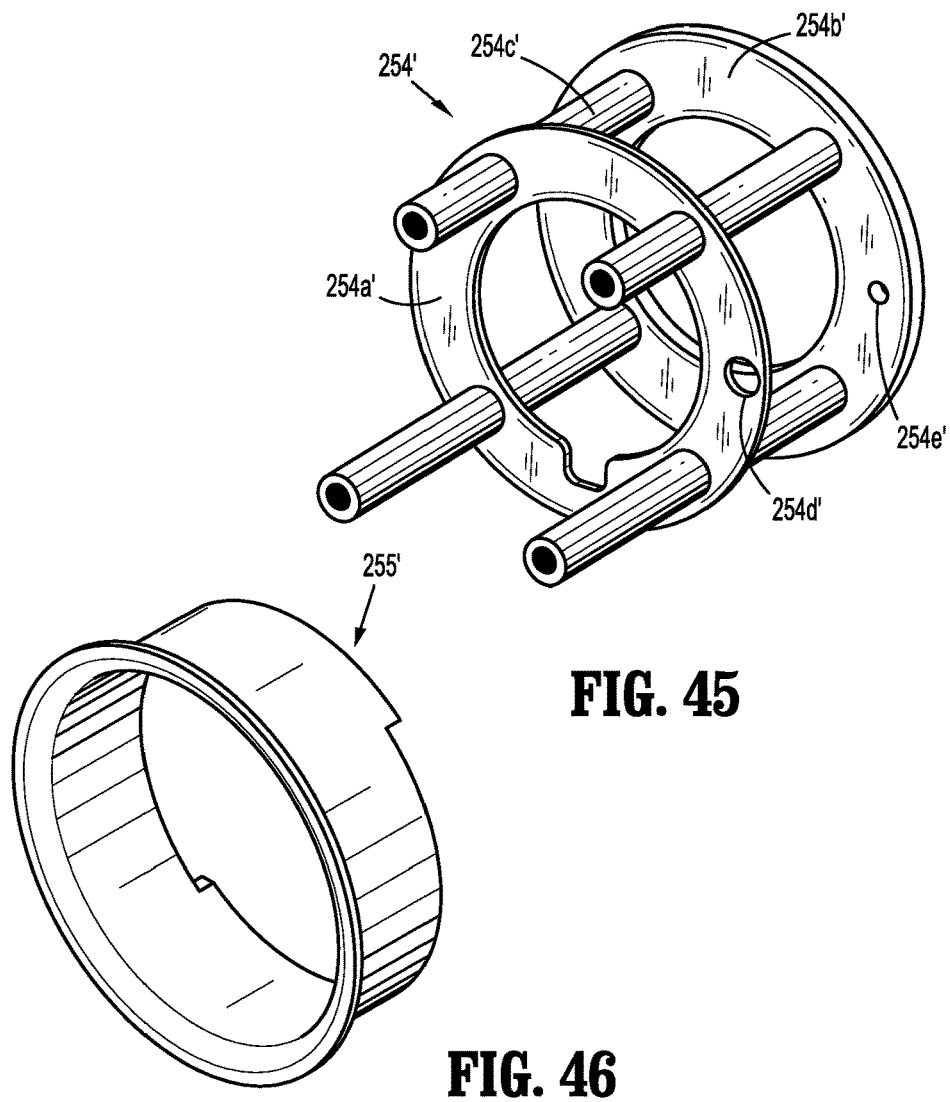
FIG. 45
FIG. 46
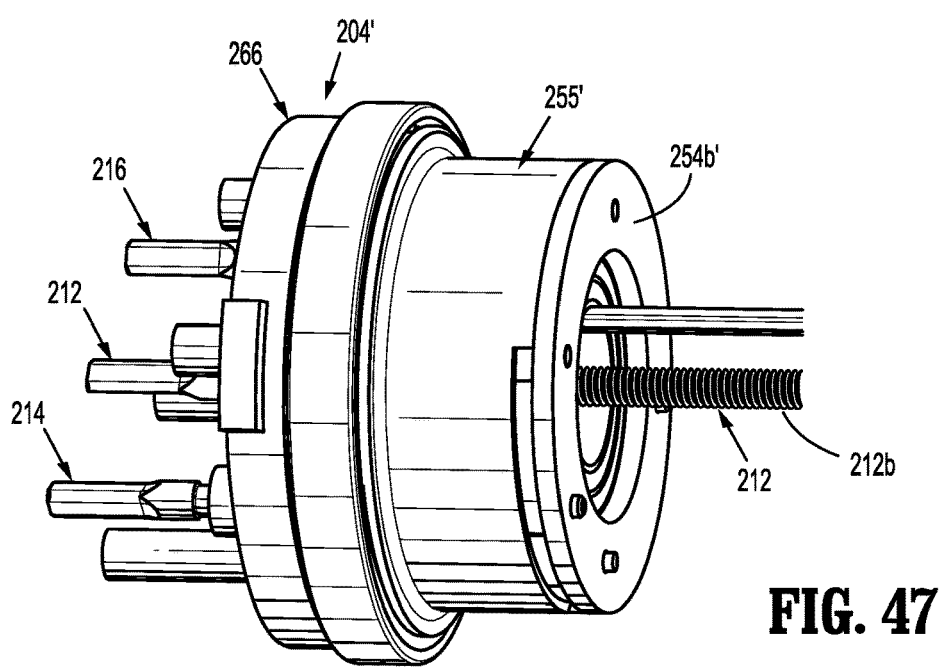
FIG. 47

ADAPTER ASSEMBLY FOR INTERCONNECTING ELECTROMECHANICAL SURGICAL DEVICES AND SURGICAL LOADING UNITS, AND SURGICAL SYSTEMS THEREOF

CROSS-REFERENCE TO RELATED APPLICATIONS

This application is a continuation of U.S. application Ser. No. 16/774,375, filed Jan. 28, 2020, now U.S. Pat. No. 11,266,404, which is a continuation of U.S. application Ser. No. 16/139,839, filed Sep. 24, 2018, now U.S. Pat. No. 10,548,596, which is a continuation of U.S. application Ser. No. 15/708,520, filed Sep. 19, 2017, now U.S. Pat. No. 10,098,637, which is a continuation of U.S. application Ser. No. 14/700,917, filed Apr. 30, 2015, now U.S. Pat. No. 9,763,661, which claims the benefit of and priority to U.S. Provisional Patent Application Ser. No. 62/017,510, filed Jun. 26, 2014, the entire disclosure of each of which is incorporated by reference herein.

BACKGROUND

The present disclosure relates to adapter assemblies for use in surgical systems. More specifically, the present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

In certain instances, an adapter assembly is used to interconnect an electromechanical surgical device with any one of a number of surgical loading units to establish a mechanical and/or electrical connection therebetween. Due to the complexity of the adapter assembly and the electromechanical surgical device, it is important to ensure that all electrical and mechanical connections therebetween can be easily, reliably and repeatedly accomplished.

Accordingly, a need exists for an adapter assembly that provides a robust way of electromechanically interconnecting with the surgical device.

SUMMARY

The present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

According to an aspect of the present disclosure, an adapter assembly for selectively interconnecting a surgical loading unit that is configured to perform a function and a surgical device that is configured to actuate the loading unit, is provided. The loading unit may include at least one axially translatable drive member, and the surgical device may include at least one rotatable drive shaft. The adapter assembly includes a housing configured and adapted for connection with the surgical device and to be in operative communication with each rotatable drive shaft of the surgical device; an outer tube having a proximal end supported by the housing and a distal end configured and adapted for connection with the loading unit, wherein the distal end of the outer tube is in operative communication with each of the axially translatable drive member of the loading unit; the force/rotation transmitting/converting assembly for interconnecting a respective one drive shaft of the surgical device and a respective one axially translatable drive member of the loading unit; and an electrical assembly supported within at least one of the housing and the outer tube. The electrical assembly includes a circuit board and an electrical connector. The electrical connector includes a connector housing coupled to a plurality of electrical contact pins. The plurality of electrical contact pins are electrically connected to the circuit board and are configured and adapted to selectively electrically connect to a complementary electrical plug of the surgical device. Each of the electrical contact pins of the plurality of electrical contact pins extends through the connector housing.

The electrical assembly may a single connector housing, where each of the electrical contact pins of the plurality of electrical contact pins extends through the single connector housing. Each of the electrical contact pins of the plurality of electrical contact pins may be fixed from moving relative to the single connector housing.

In disclosed embodiments, the connector housing is secured to the plurality of electrical contact pins via overmolding. Each of the electrical contact pins of the plurality of electrical contact pins may include a hole extending therethrough, such that a portion of the connector housing extends through the hole of each of the electrical contact pins of the plurality of electrical contact pins.

A proximal portion of each of the electrical contact pins of the plurality of electrical contact pins may include a rectangular cross-section.

The connector housing may include at least one projection extending from a surface thereof. A distal face of the at least one projection is configured to abut the circuit board when the plurality of electrical contact pins are electrically connected to the circuit board. A proximal face of the at least one projection is configured to abut a surface of proximal cap to prevent unintended disengagement between the electrical connector and the circuit board.

In disclosed embodiments, the electrical assembly includes a strain gauge supported on and electrically connected to the circuit board. A rotatable drive shaft of the surgical device extends through the strain gauge. The electrical assembly may also include a slip ring disposed about a portion of a first force/rotation transmitting/converting assembly. The slip ring is in electrical connection with the circuit board, and includes an electrical contact supported therein for maintaining electrical contact with at least one electrical component within the adapter assembly.

The present disclosure also relates to an electrical assembly for use with an adapter assembly for selectively interconnecting a surgical loading unit that is configured to perform a function and a surgical device that is configured to actuate the loading unit. The electrical assembly includes a circuit board and an electrical connector. The electrical connector includes a connector housing coupled to a plurality of electrical contact pins. The plurality of electrical contact pins are electrically connectable to the circuit board and are configured and adapted to selectively electrically connect to a complementary electrical plug of a surgical device. Each of the electrical contact pins of the plurality of electrical contact pins extends through the connector housing.

In disclosed embodiments, the electrical assembly includes a single connector housing, such that each of the electrical contact pins of the plurality of electrical contact pins extends through the single connector housing. Here, each of the electrical contact pins of the plurality of electrical contact pins is fixed from moving relative to the single connector housing.

It is also disclosed that the connector housing is secured to the plurality of electrical contact pins via over-molding. Also, each of the electrical contact pins of the plurality of electrical contact pins may include a hole extending therethrough, such that a portion of the connector housing extends through the hole of each of the electrical contact pins of the plurality of electrical contact pins.

A proximal portion of each of the electrical contact pins of the plurality of electrical contact pins may include a rectangular cross-section.

In disclosed embodiments, the connector housing includes at least one projection extending from a surface thereof. A distal face of the at least one projection is configured to abut the circuit board when the plurality of electrical contact pins are electrically connected to the circuit board. A proximal face of the at least one projection is configured to abut a surface of proximal cap 210 to prevent unintended disengagement between the electrical connector and the circuit board.

It is further disclosed that the electrical assembly further comprises a strain gauge supported on and electrically connected to the circuit board. Additionally, the electrical assembly may also include a slip ring disposed in electrical connection with the circuit board, such that the slip ring includes an electrical contact supported therein for maintaining electrical contact with at least one electrical component within the adapter assembly.

BRIEF DESCRIPTION OF THE DRAWINGS

Embodiments of the present disclosure are described herein with reference to the accompanying drawings, wherein:

FIG. 2A is a front, perspective view of the adapter assembly of the present disclosure;

FIG. 2B is a rear, perspective view of the adapter assembly of FIG. 2A;

FIG. 3 is a top plan view of the adapter assembly of FIGS. 2A and 2B;

FIG. 4 is a side, elevational view of the adapter assembly of FIGS. 2A and 2B;

FIG. 45 is a perspective view of a bracket assembly of the inner housing assembly of FIGS. 43 and 44;

FIG. 46 is a perspective view of a reinforcing sleeve for use with the inner housing assembly of FIGS. 43 and 44;

FIG. 47 is a perspective view of the inner housing assembly of FIGS. 43 and 44, illustrating the reinforcing sleeve of FIG. 46 supported thereon.

DETAILED DESCRIPTION OF EMBODIMENTS

Figure 1A:
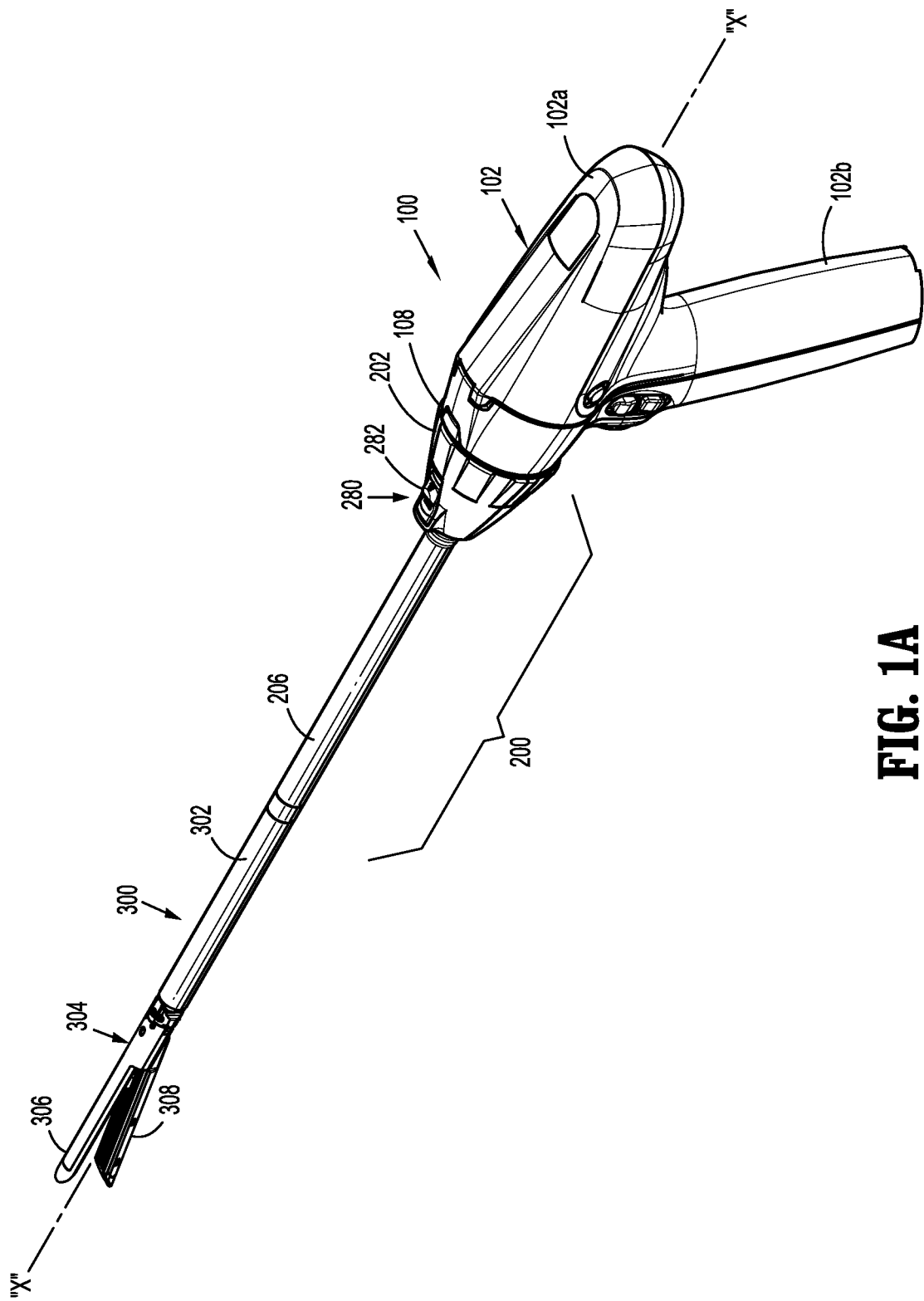
FIG. 1A is a perspective view of an adapter assembly, in accordance with an embodiment of the present disclosure, interconnected between an exemplary electromechanical surgical device and an end effector assembly.

Embodiments of the presently disclosed surgical devices, adapter assemblies, and loading unit detection assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument.

Figure 48:
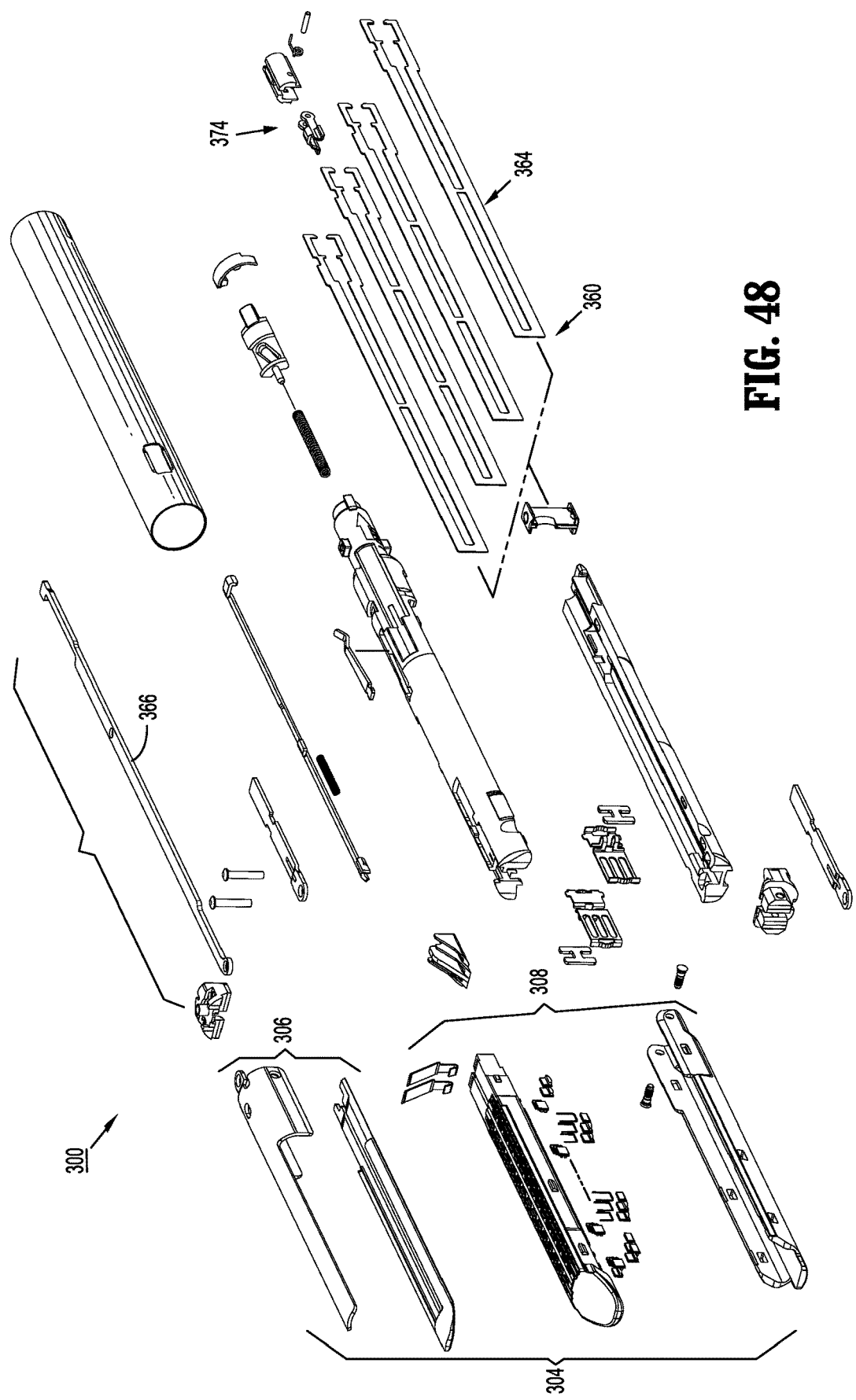
FIG. 48 is a perspective view, with parts separated, of an exemplary loading unit for use with the surgical device and the adapter of the present disclosure.

As illustrated in FIG. 1A, surgical device 100 is configured for selective connection with an adapter assembly 200, and, in turn, adapter assembly 200 is configured for selective connection with a loading unit 300 (e.g., an end effector, or multiple- or single-use loading unit; see FIG. 48). Surgical device 100 and adapter assembly 200, together, may comprise an electromechanical surgical system that is configured and adapted to selectively connect with a loading unit 300 and to actuate loading unit 300.

Figure 1B:
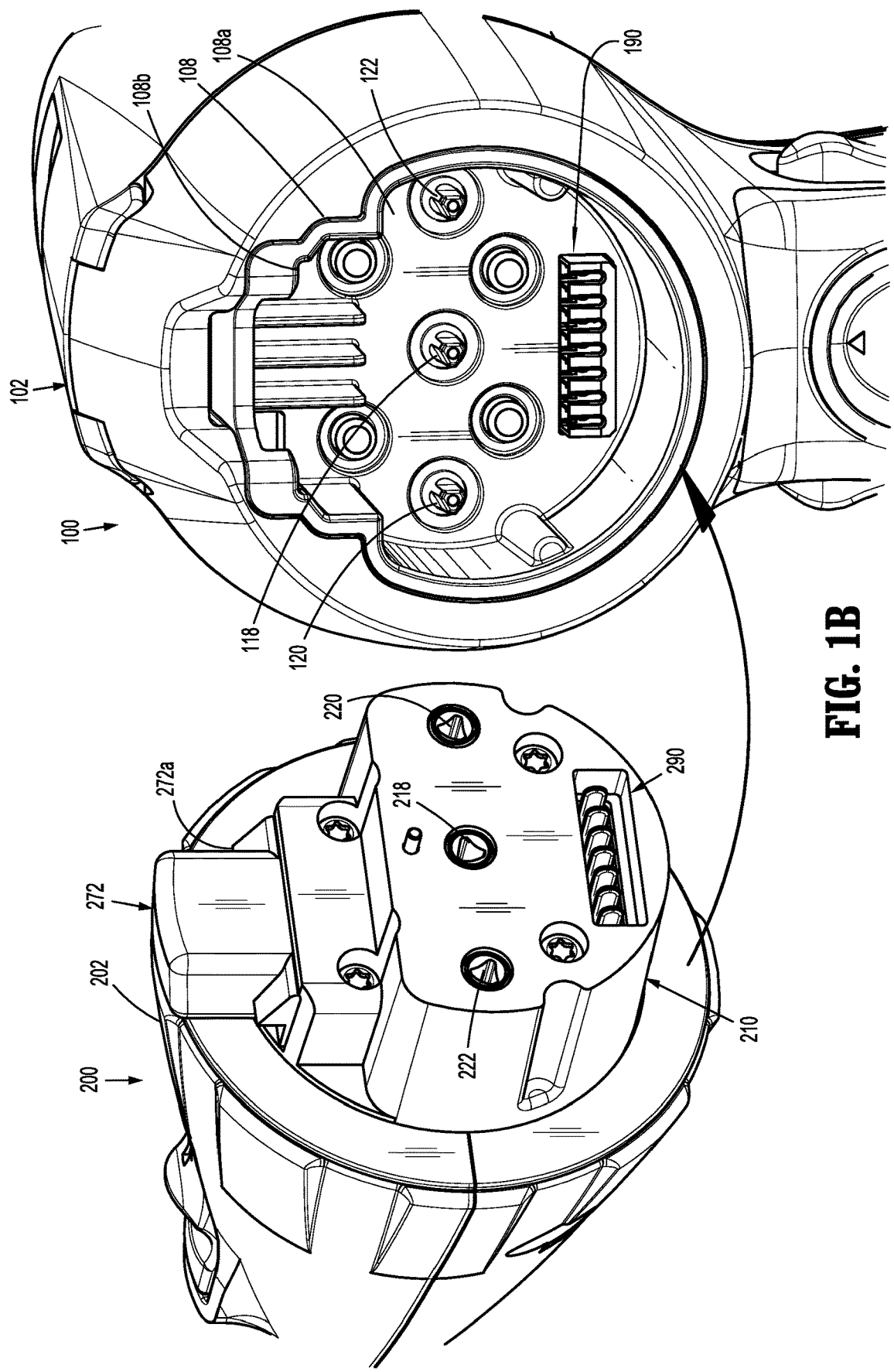
FIG. 1B is a perspective view illustrating an attachment of a proximal end of the adapter assembly to a distal end of the electromechanical surgical device.

As illustrated in FIGS. 1A and 1B, surgical device 100 includes a handle housing 102 including a circuit board (not shown), and a drive mechanism (not shown) is situated therein. The circuit board is configured to control the various operations of surgical device 100. Handle housing 102 defines a cavity therein (not shown) for selective removable receipt of a rechargeable battery (not shown) therein. The battery is configured to supply power to any of the electrical components of surgical device 100.

Handle housing 102 includes an upper housing portion 102a which houses various components of surgical device 100, and a lower hand grip portion 102b extending from upper housing portion 102a. Lower hand grip portion 102b may be disposed distally of a proximal-most end of upper housing portion 102a. The location of lower housing portion 102b relative to upper housing portion 102a is selected to balance a weight of a surgical device 100 that it is connected to or supporting adapter assembly 200 and/or end effector 300.

Handle housing 102 provides a housing in which the drive mechanism is situated. The drive mechanism is configured to drive shafts and/or gear components in order to perform the various operations of surgical device 100. In particular, the drive mechanism is configured to drive shafts and/or gear components in order to selectively move a tool assembly 304 of loading unit 300 (see FIGS. 1A and 48) relative to a proximal body portion 302 of loading unit 300, to rotate loading unit 300 about a longitudinal axis "X" (see FIG. 1A) relative to handle housing 102, to move/approximate an anvil assembly 306 and/or a cartridge assembly 308 of loading unit 300 relative to one another, and/or to fire a stapling and cutting cartridge within cartridge assembly 308 of loading unit 300.

Figure 5:
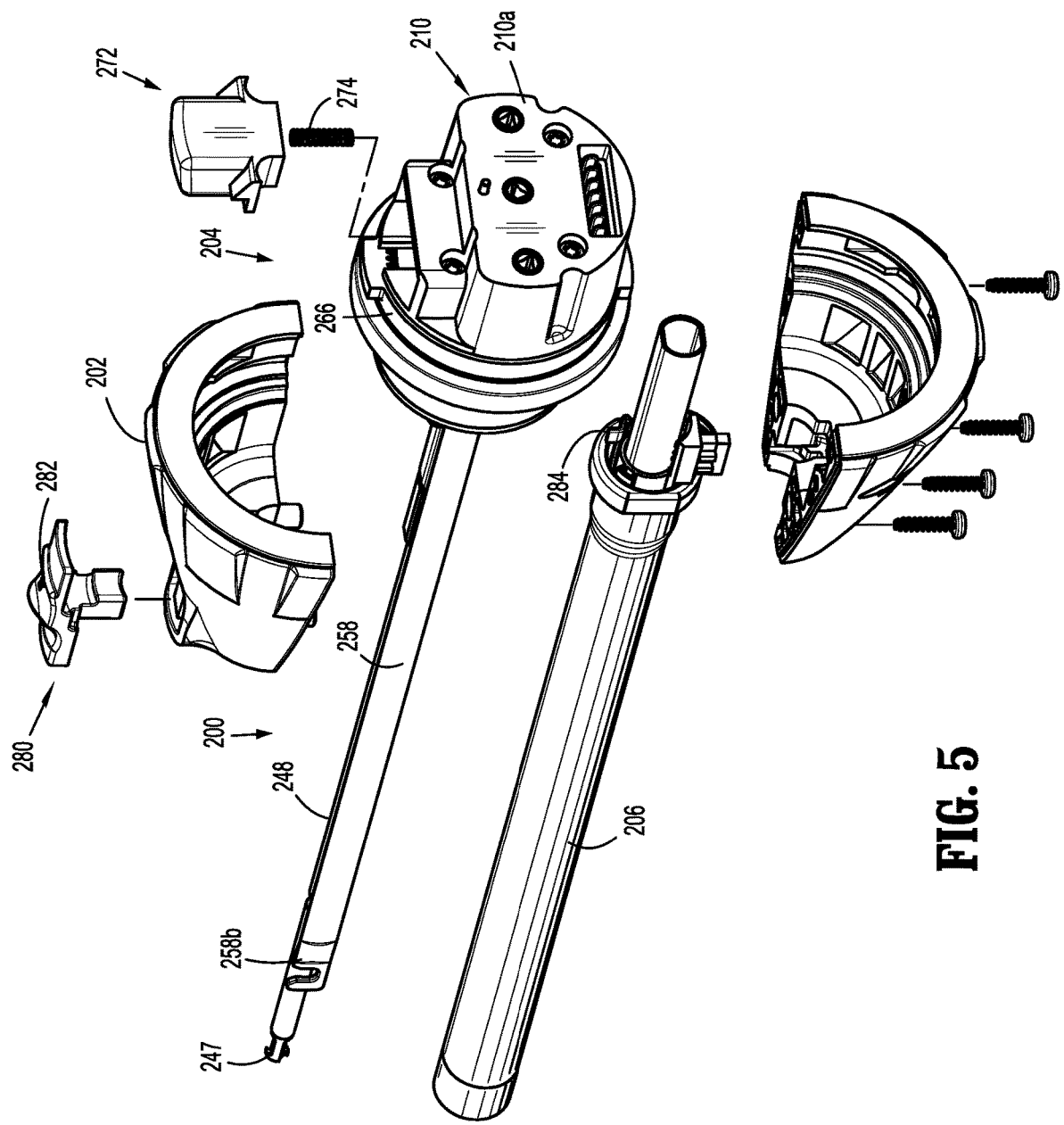
FIG. 5 is a rear, perspective view of the adapter assembly of FIGS. 2A and 2B, with some parts thereof separated.

As illustrated in FIG. 1B, handle housing 102 defines a connecting portion 108 configured to accept a corresponding drive coupling assembly 210 of adapter assembly 200. Specifically, connecting portion 108 of surgical device 100 has a recess 108a that receives a proximal cap 210a (FIGS. 5 and 6) of drive coupling assembly 210 of adapter assembly 200 when adapter assembly 200 is mated to surgical device 100. Connecting portion 108 houses three rotatable drive connectors 118, 120, 122 which are arranged in a common plane or line with one another.

When adapter assembly 200 is mated to surgical device 100, each of rotatable drive connectors 118, 120, 122 of surgical device 100 couples with a corresponding rotatable connector sleeve 218, 220, 222 of adapter assembly 200 (see FIG. 1B). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter assembly 200.

The mating of drive connectors 118, 120, 122 of surgical device 100 with connector sleeves 218, 220, 222 of adapter assembly 200 allows rotational forces to be independently transmitted via each of the three respective connector interfaces. The drive connectors 118, 120, 122 of surgical device 100 are configured to be independently rotated by the drive mechanism of surgical device 100. In this regard, a function selection module (not shown) of the drive mechanism selects which drive connector or connectors 118, 120, 122 of surgical device 100 is to be driven by the motor of surgical device 100.

Since each of drive connectors 118, 120, 122 of surgical device 100 has a keyed and/or substantially non-rotatable interface with respective connector sleeves 218, 220, 222 of adapter assembly 200, when adapter assembly 200 is coupled to surgical device 100, rotational force(s) are selectively transferred from drive connectors of surgical device 100 to adapter assembly 200.

The selective rotation of drive connector(s) 118, 120 and/or 122 of surgical device 100 allows surgical device 100 to selectively actuate different functions of loading unit 300. For example, selective and independent rotation of first drive connector 118 of surgical device 100 corresponds to the selective and independent opening and closing of tool assembly 304 of loading unit 300, and driving of a stapling/cutting component of tool assembly 304 of loading unit 300. As an additional example, the selective and independent rotation of second drive connector 120 of surgical device 100 corresponds to the selective and independent articulation of tool assembly 304 of loading unit 300 transverse to longitudinal axis "X" (see FIG. 1A). Additionally, for instance, the selective and independent rotation of third drive connector 122 of surgical device 100 corresponds to the selective and independent rotation of loading unit 300 about longitudinal axis "X" (see FIG. 1A) relative to handle housing 102 of surgical device 100.

As illustrated in FIG. 1A, handle housing 102 supports a plurality of finger-actuated control buttons, rocker devices and the like for activating various functions of surgical device 100.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, now U.S. Pat. No. 10,588,629, the entire content of each of which being incorporated herein by reference, for a detailed description of various internal components of and operation of exemplary electromechanical, hand-held, powered surgical instrument 100.

With particular reference to FIGS. 1B-2B, adapter assembly 200 includes an outer knob housing 202 and an outer tube 206 extending from a distal end of knob housing 202. Knob housing 202 and outer tube 206 are configured and dimensioned to house the components of adapter assembly 200. Outer tube 206 is dimensioned for endoscopic insertion, in particular, outer tube 206 is passable through a typical trocar port, cannula or the like. Knob housing 202 is dimensioned to not enter the trocar port, cannula of the like.

Knob housing 202 is configured and adapted to connect to connecting portion 108 of handle housing 102 of surgical device 100.

Adapter assembly 200 is configured to convert a rotation of either of drive connectors 118, 120 and 122 of surgical device 100 into axial translation useful for operating a drive assembly 360 and an articulation link 366 of loading unit 300, as illustrated in FIG. 48 and as will be described in greater detail below. As illustrated in FIGS. 5, 6, 13, 14, 17, 18, 20, 25-34 and 37-40, adapter assembly 200 includes a proximal inner housing assembly 204 rotatably supporting a first rotatable proximal drive shaft 212, a second rotatable proximal drive shaft 214, and a third rotatable proximal drive shaft 216 therein. Each proximal drive shaft 212, 214, 216 functions as a rotation receiving member to receive rotational forces from respective drive shafts of surgical device 100, as described in greater detail below.

As described briefly above, inner housing assembly 210 of shaft assembly 200 is also configured to rotatably support first, second and third connector sleeves 218, 220 and 222, respectively, arranged in a common plane or line with one another. Each of connector sleeves 218, 220, 222 is configured to mate with respective first, second and third drive connectors 118, 120, 122 of surgical device 100, as described above. Each of connector sleeves 218, 220, 222 is further configured to mate with a proximal end of respective first, second and third proximal drive shafts 212, 214, 216.

Inner housing assembly 210 also includes, as illustrated in FIGS. 6, 17, 27 and 28, a first, a second and a third biasing member 224, 226 and 228 disposed distally of respective first, second and third connector sleeves 218, 220, 222. Each of biasing members 224, 226 and 228 is disposed about respective first, second and third rotatable proximal drive shaft 212, 214 and 216. Biasing members 224, 226 and 228 act on respective connector sleeves 218, 220 and 222 to help maintain connector sleeves 218, 220 and 222 engaged with the distal end of respective drive rotatable drive connectors 118, 120, 122 of surgical device 100 when adapter assembly 200 is connected to surgical device 100.

In particular, first, second and third biasing members 224, 226 and 228 function to bias respective connector sleeves 218, 220 and 222 in a proximal direction. In this manner, during assembly of adapter assembly 200 to surgical device 100, if first, second and or third connector sleeves 218, 220 and/or 222 is/are misaligned with the drive connectors 118, 120, 122 of surgical device 100, first, second and/or third biasing member(s) 224, 226 and/or 228 are compressed. Thus, when surgical device 100 is operated, drive connectors 118, 120, 122 of surgical device 100 will rotate and first, second and/or third biasing member(s) 224, 226 and/or 228 will cause respective first, second and/or third connector sleeve(s) 218, 220 and/or 222 to slide back proximally, effectively coupling drive connectors 118, 120, 122 of surgical device 100 to first, second and/or third proximal drive shaft(s) 212, 214 and 216 of inner housing assembly 210.

Adapter assembly 200 includes a plurality of force/rotation transmitting/converting assemblies, each disposed within inner housing assembly 204 and outer tube 206. Each force/rotation transmitting/converting assembly is configured and adapted to transmit/convert a speed/force of rotation (e.g., increase or decrease) of first, second and third rotatable drive connectors 118, 120 and 122 of surgical instrument 100 before transmission of such rotational speed/force to loading unit 300.

Figure 6:
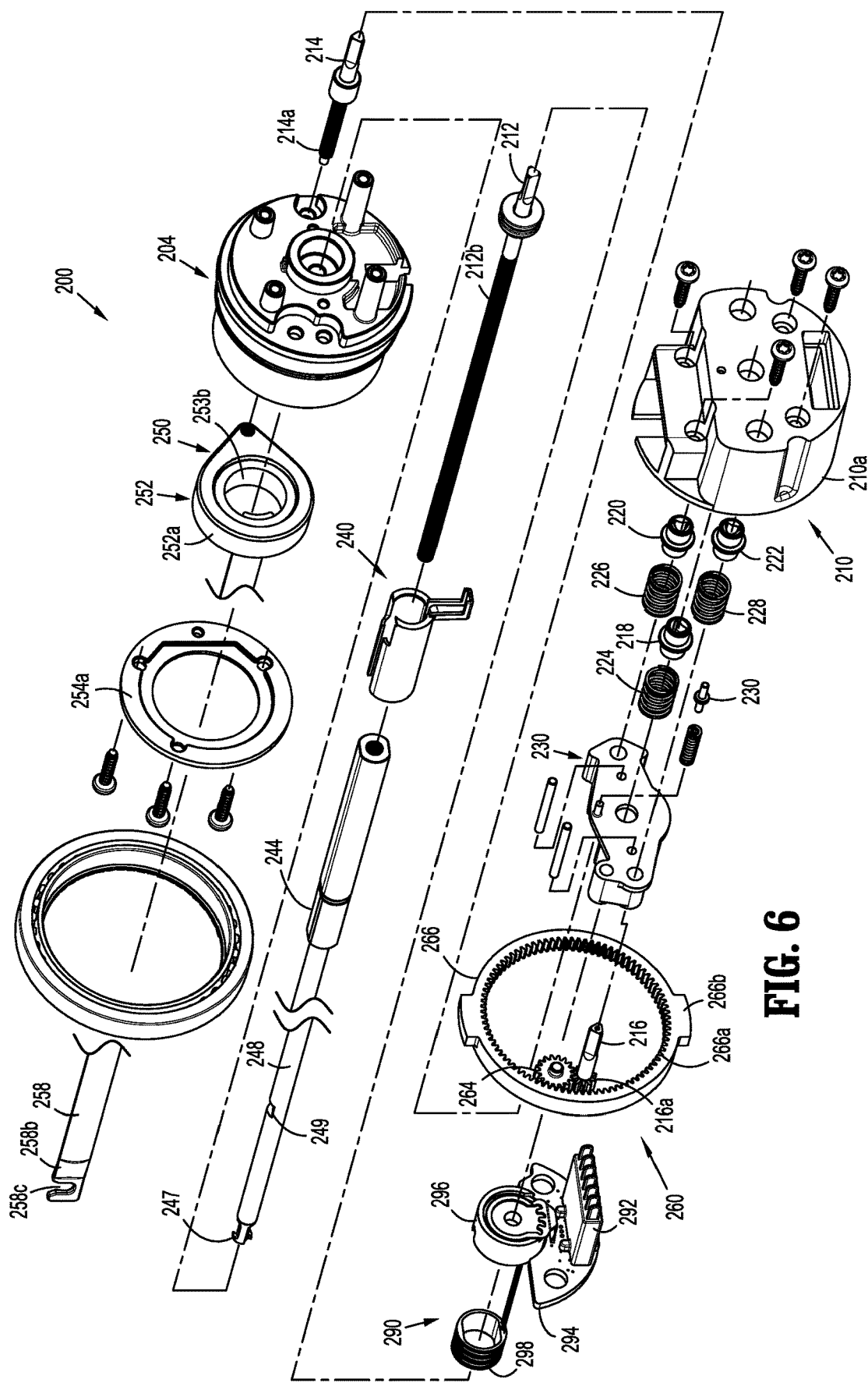
FIG. 6 is a rear, perspective view of the adapter assembly of FIGS. 2A and 2B, with most parts thereof separated.
Figure 7:
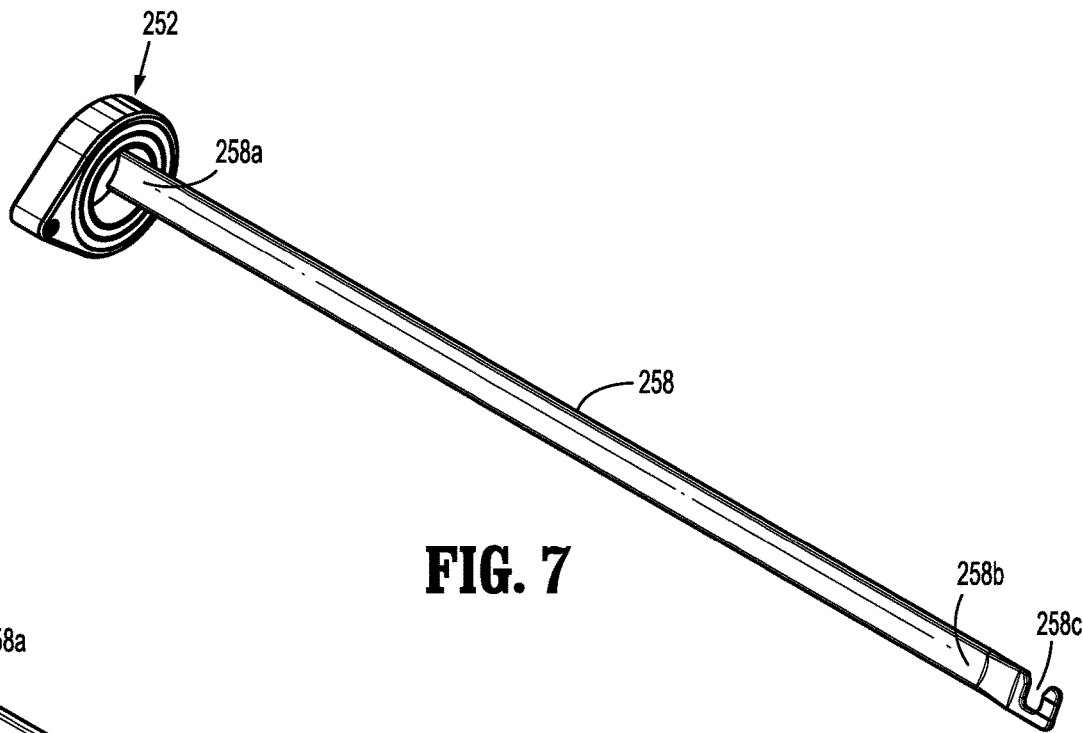
FIG. 7 is a perspective view of an articulation assembly of the adapter assembly of FIGS. 2A and 2B.
Figure 8:
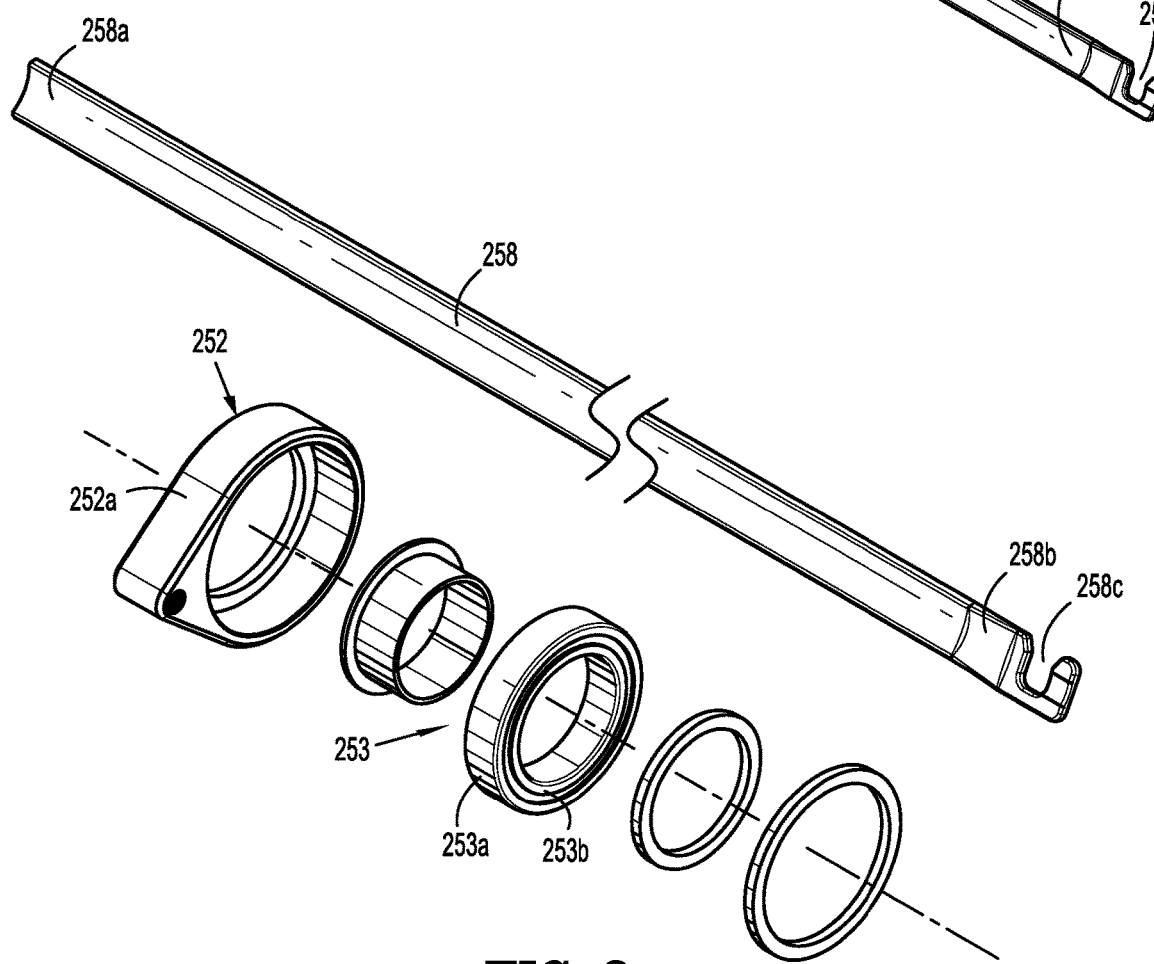
FIG. 8 is an enlarged, perspective view, with parts separated, of the articulation assembly of FIG. 7.
Figure 9:
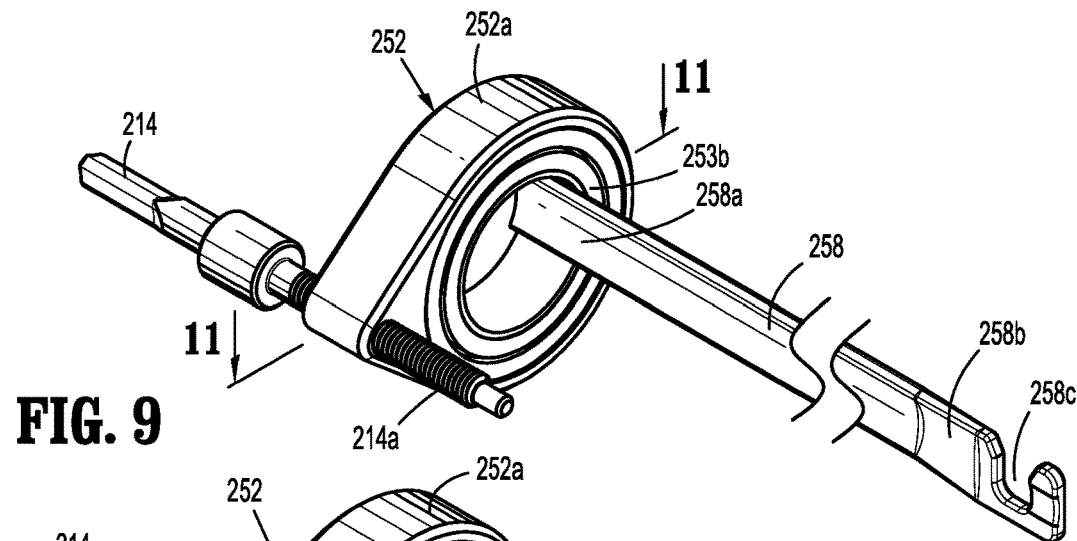
FIG. 9 is a perspective view of the articulation assembly of FIG. 7, shown in a first orientation.
Figure 10:
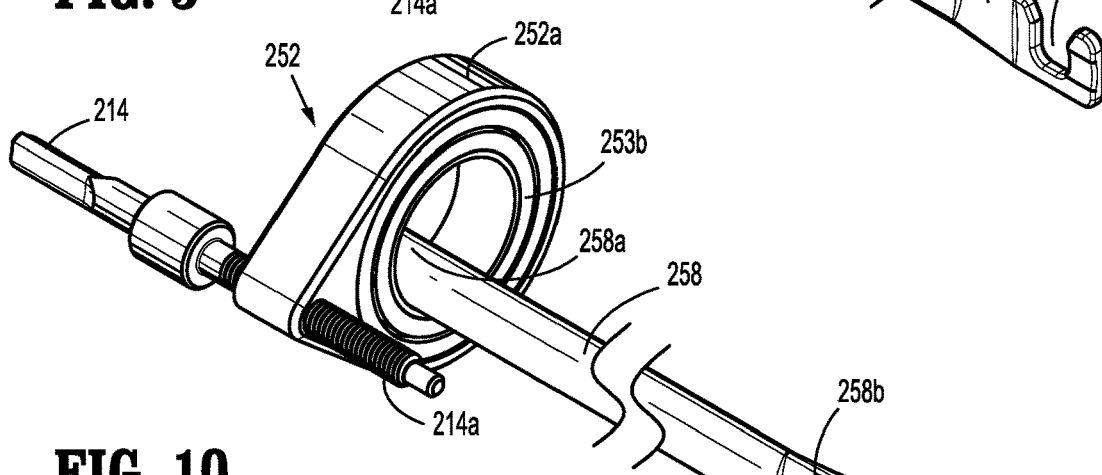
FIG. 10 is a perspective view of the articulation assembly of FIG. 7, shown in a second orientation.
Figure 11:
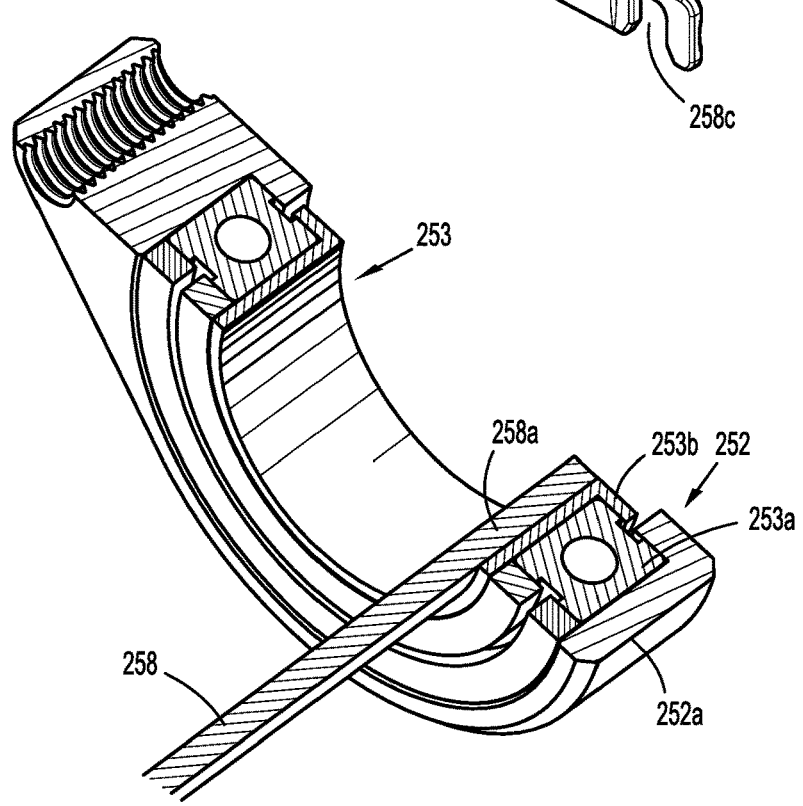
FIG. 11 is a cross-sectional view as taken along section line 11-11 of FIG. 9.
Figure 12A:
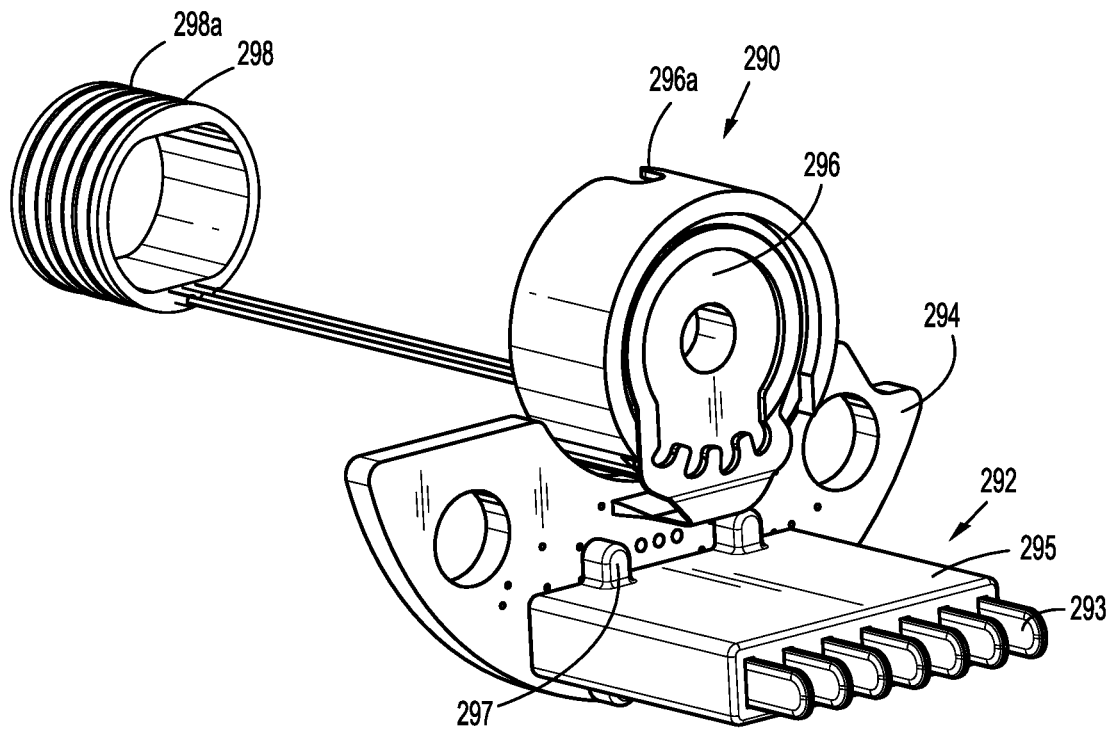
FIG. 12A is a perspective view of an electrical assembly of the adapter assembly of FIGS. 2A and 2B.
Figure 12B:
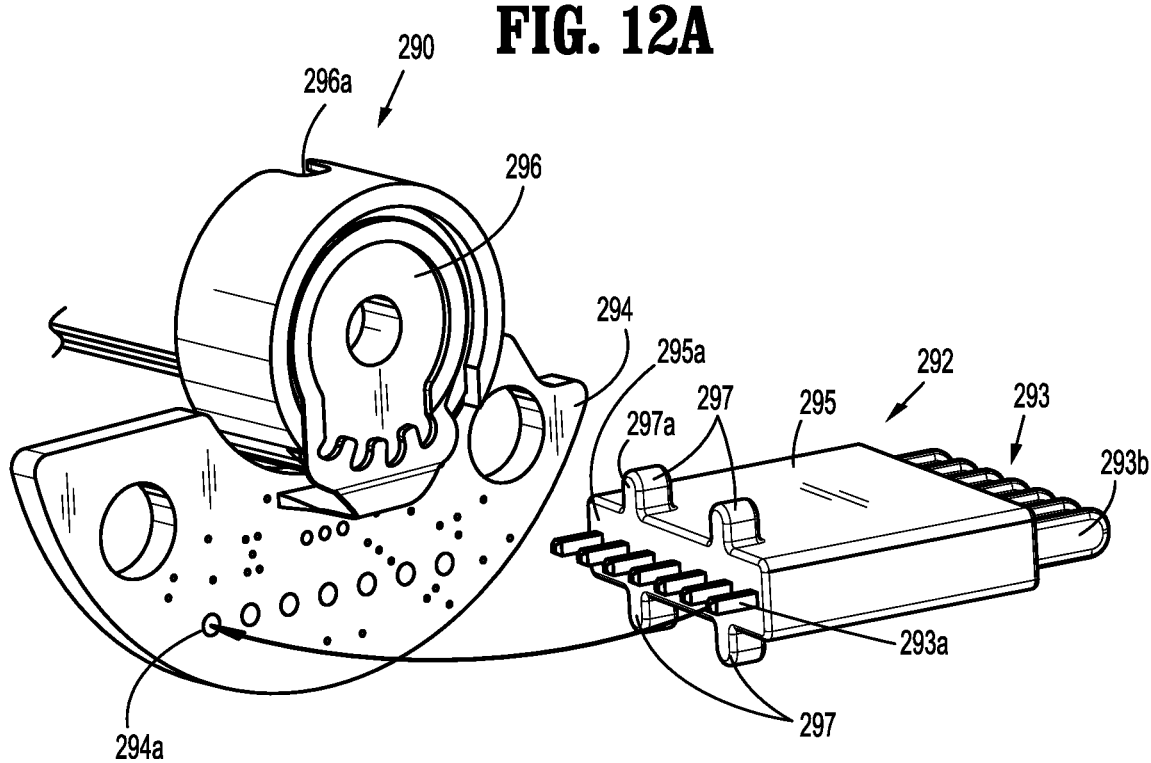
FIG. 12B is a perspective view of the electrical assembly of FIG. 12A showing a connector housing separated from a circuit board.
Figure 12C:
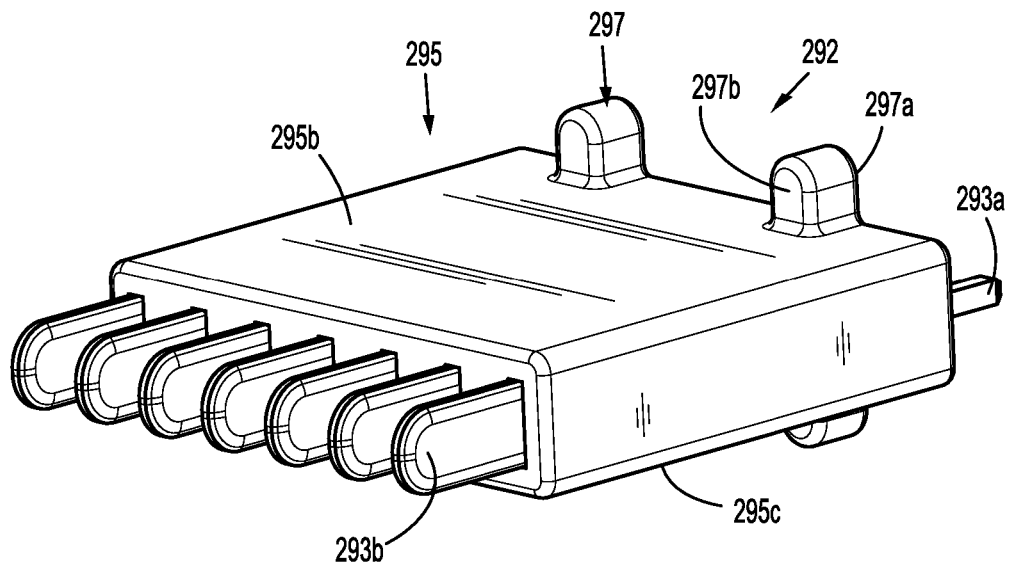
FIG. 12C is a perspective view of the connector housing of FIG. 12B.
Figure 12D:
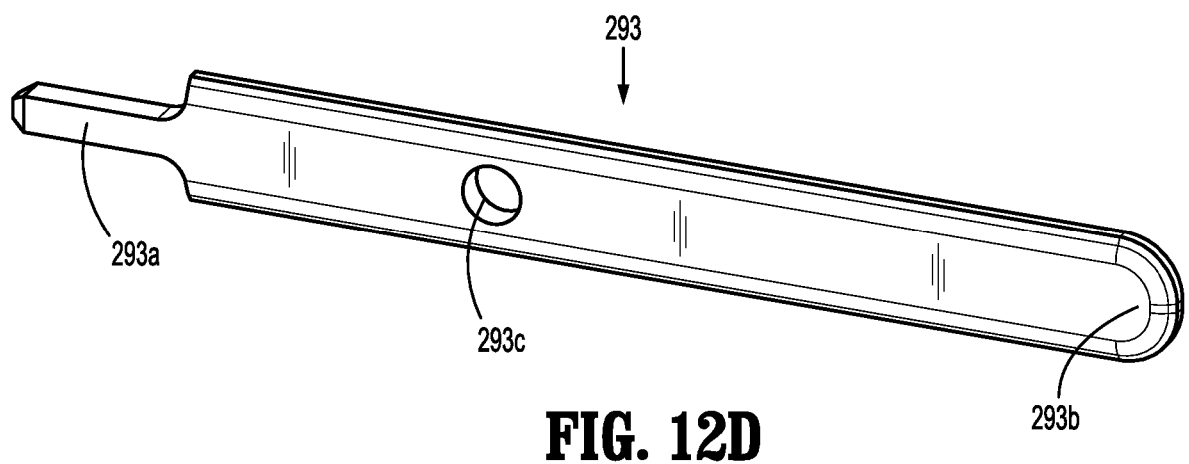
FIG. 12D is a perspective view of an electrical contact pin of the connector housing of FIGS. 12B-12C.
Figure 13:
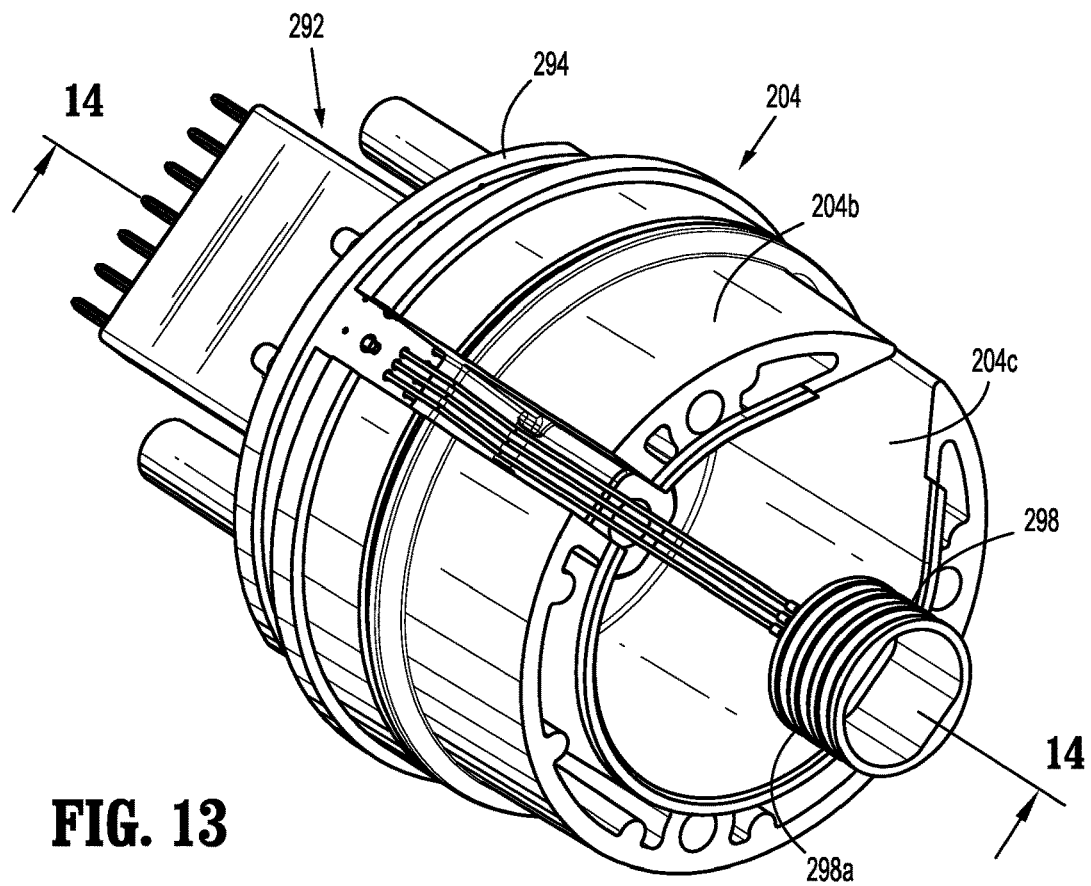
FIG. 13 is a perspective view of the electrical assembly of FIG. 12A shown connected to the core housing of the adapter assembly of FIGS. 2A and 2B.
Figure 14:
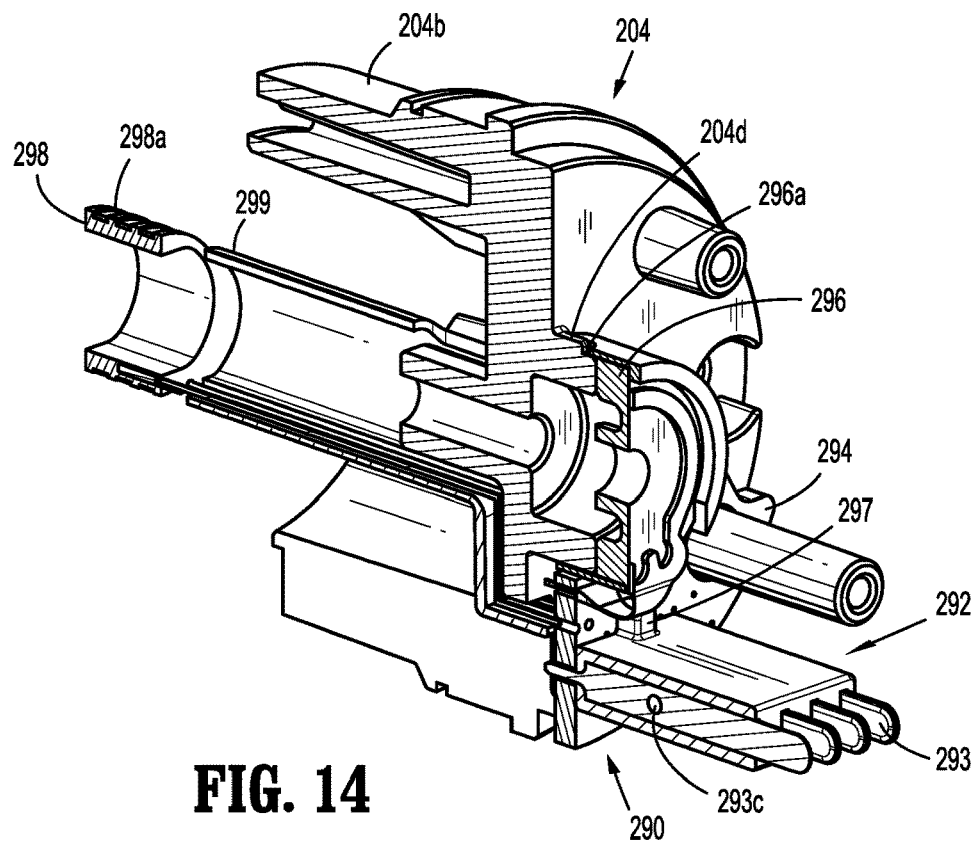
FIG. 14 is a cross-sectional view as taken along section line 14-14 of FIG. 13.
Figure 15:
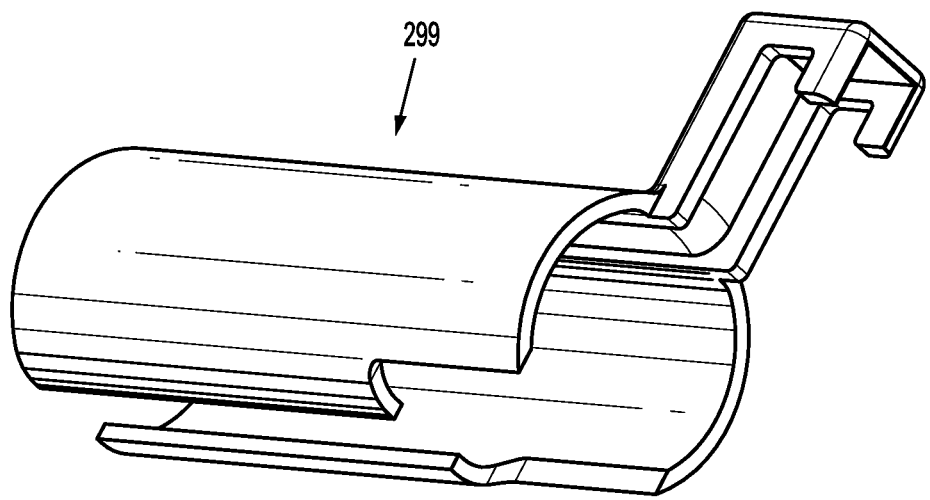
FIG. 15 is a perspective view of a slip ring cannula or sleeve of the adapter assembly of FIGS. 2A and 2B.
Figure 16:
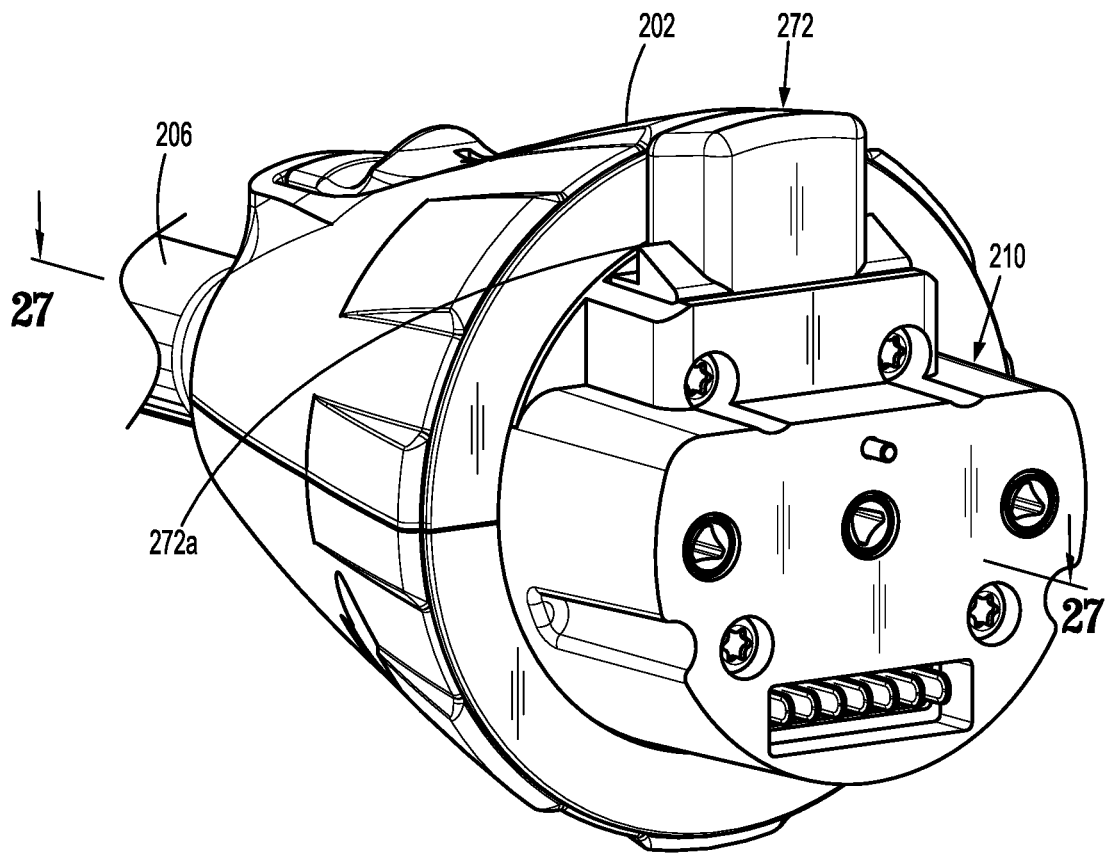
FIG. 16 is an enlarged view of the indicated area of detail of FIG. 2B, illustrating an inner housing assembly of the adapter assembly of FIGS. 2A and 2B.
Figure 17:
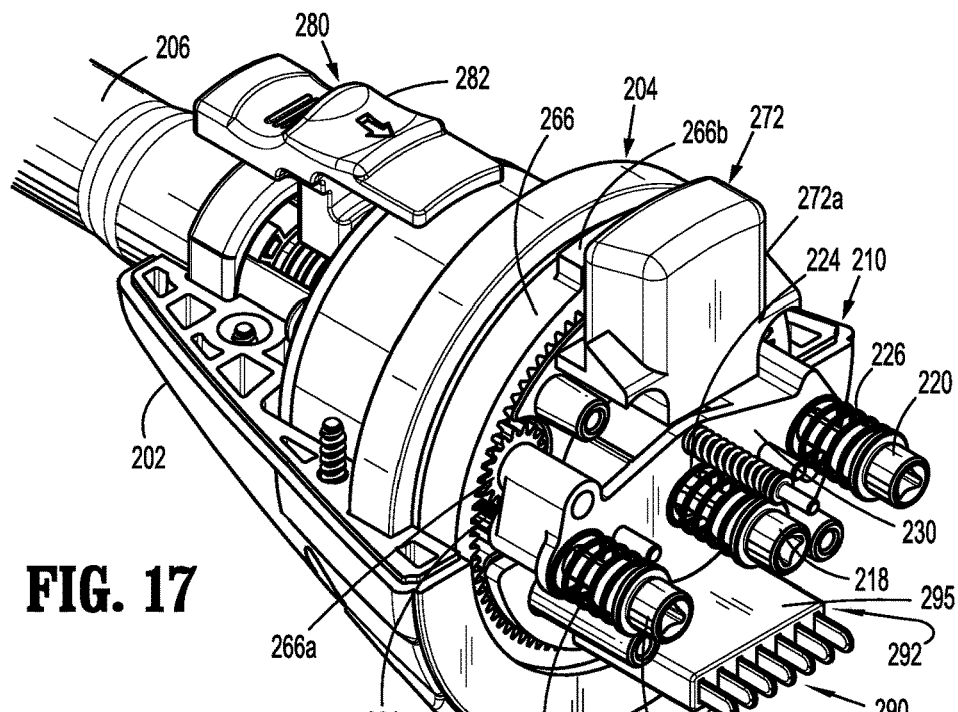
FIG. 17 is a rear, perspective view of the inner housing assembly of FIG. 16 with an outer knob housing half-section and a proximal cap removed therefrom.
Figure 18:
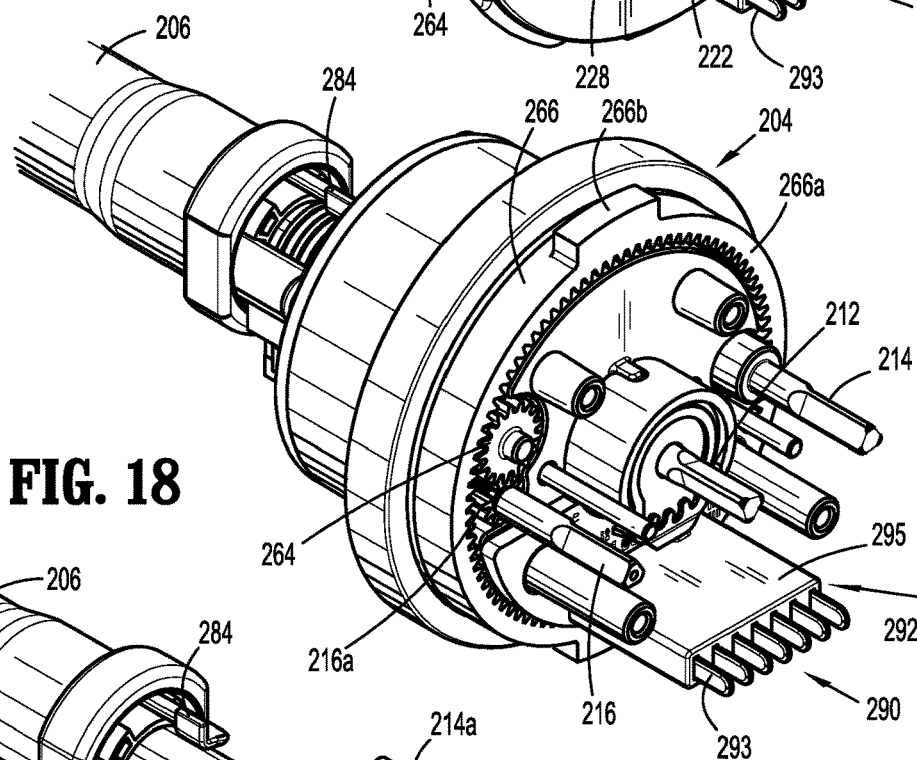
FIG. 18 is a rear, perspective view of the inner housing assembly of FIG. 16 with the outer knob housing, the proximal cap and a bushing plate removed therefrom.
Figure 19:
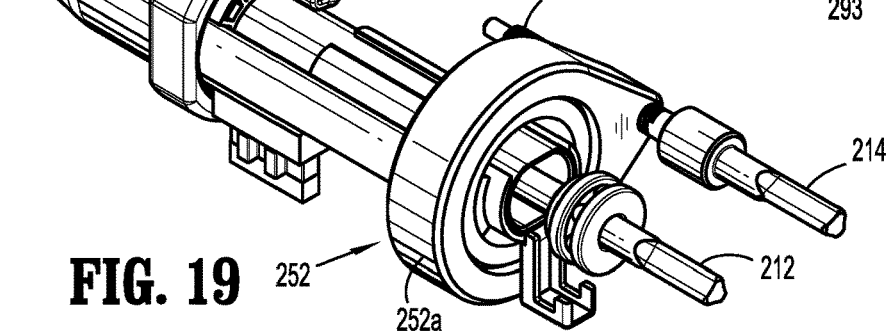
FIG. 19 is a rear, perspective view of the inner housing assembly of FIG. 16 with the outer knob housing, the proximal cap, the bushing plate and an inner housing removed therefrom.
Figure 20:
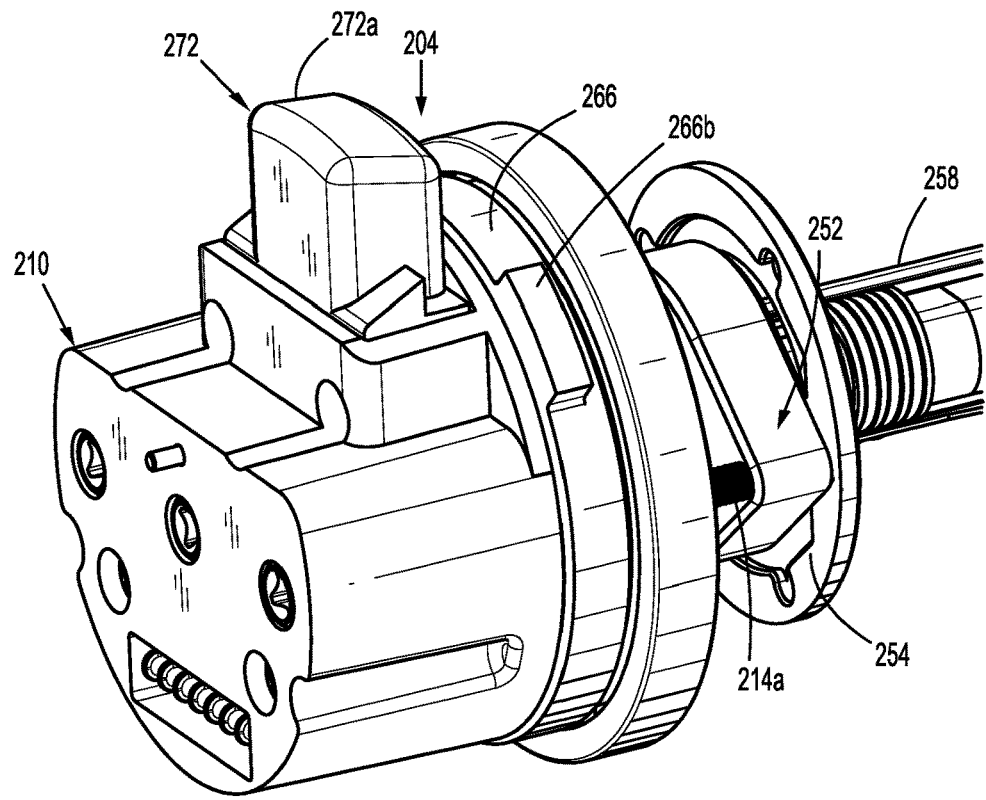
FIG. 20 is a rear, perspective view of the an alternative embodiment of inner housing assembly similar to that shown in FIG. 16 with the outer knob housing and the proximal inner housing removed therefrom.
Figure 21:
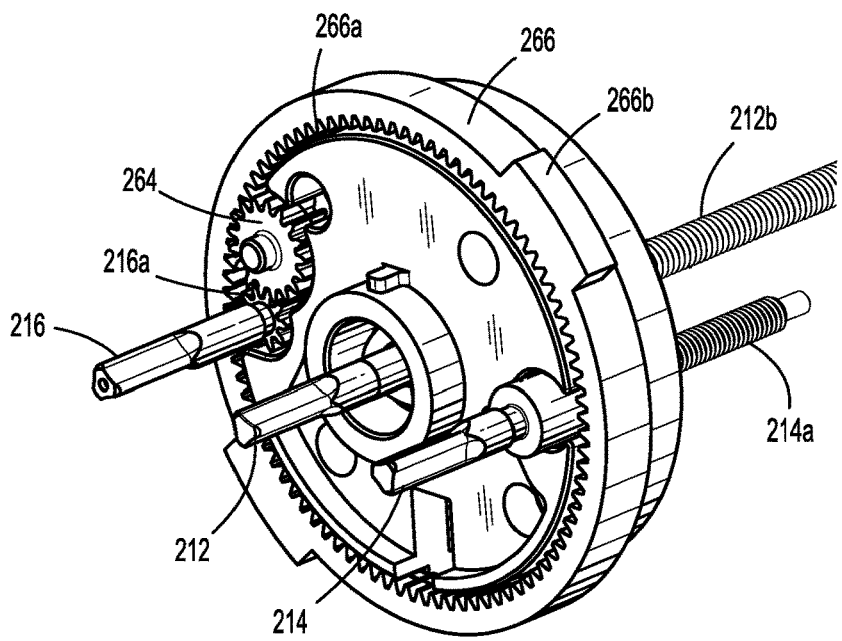
FIG. 21 is a rear, perspective view of the inner housing assembly of FIG. 20 with the outer knob housing, the proximal inner housing and the articulation assembly removed therefrom.
Figure 22:
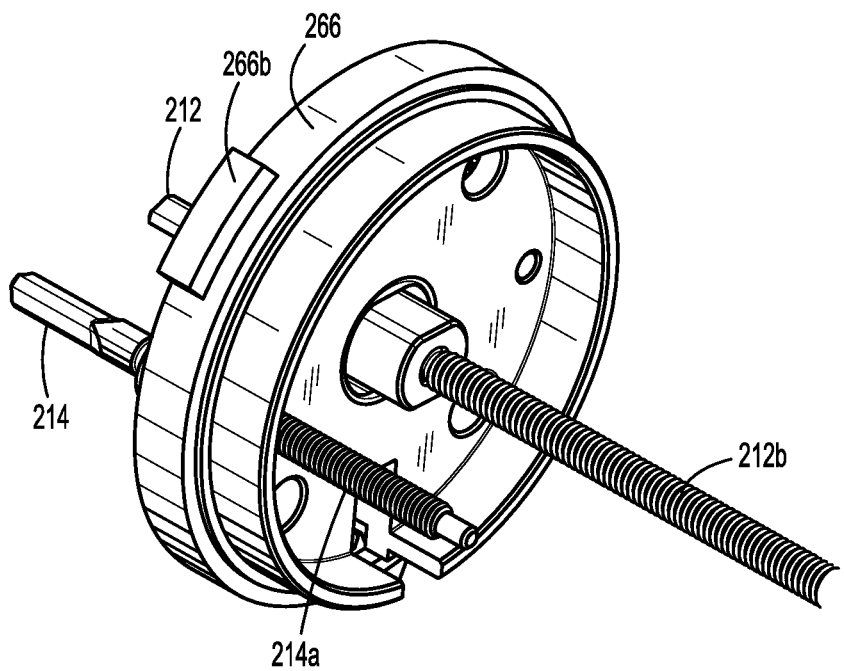
FIG. 22 is a front, perspective view of the inner housing assembly of FIG. 20 with the outer knob housing, the proximal inner housing and the articulation assembly removed therefrom.
Figure 23:
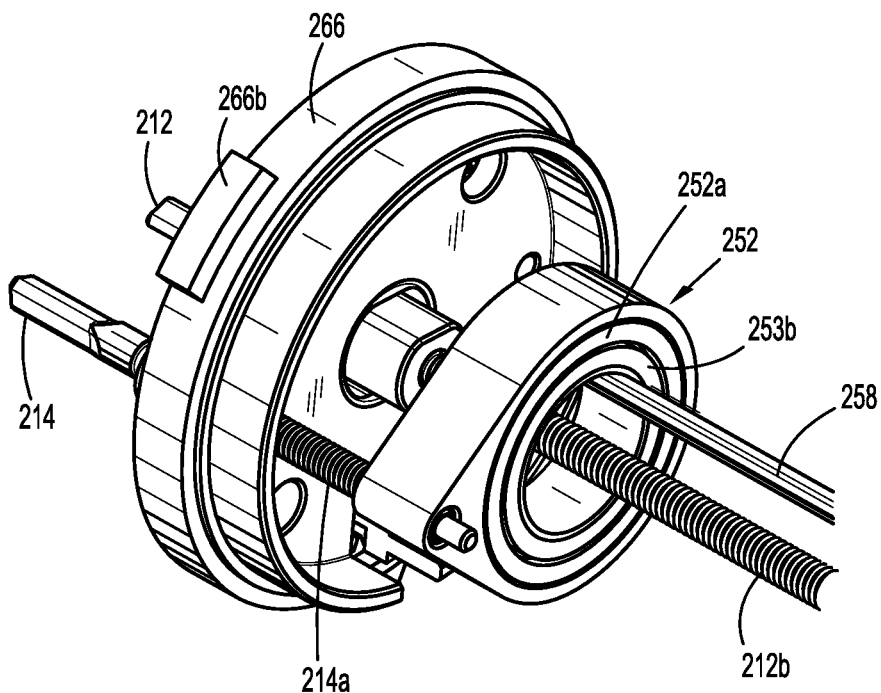
FIG. 23 is a front, perspective view of the inner housing assembly of FIG. 20 with the outer knob housing and the proximal inner housing removed therefrom.
Figure 24:
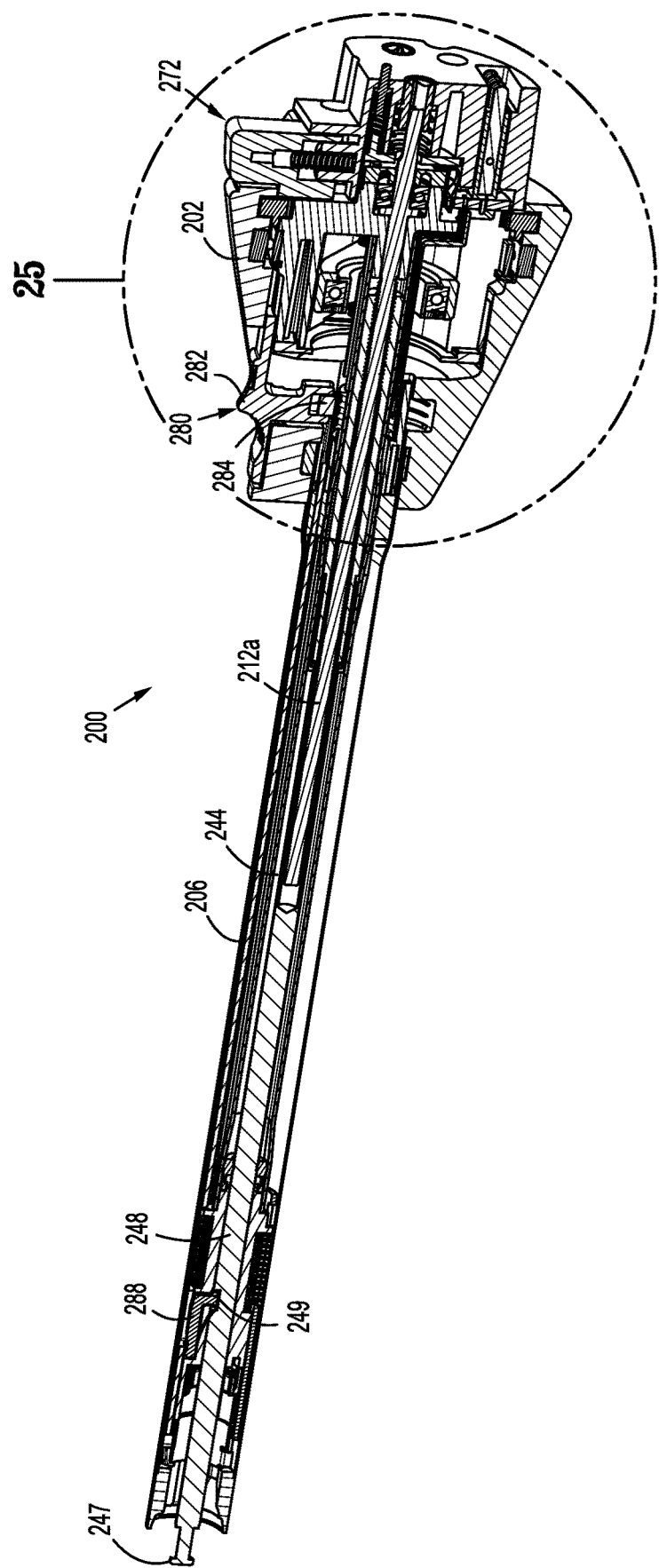
FIG. 24 is a cross-sectional view as taken along section line 24-24 of FIG. 2B.
Figure 25:
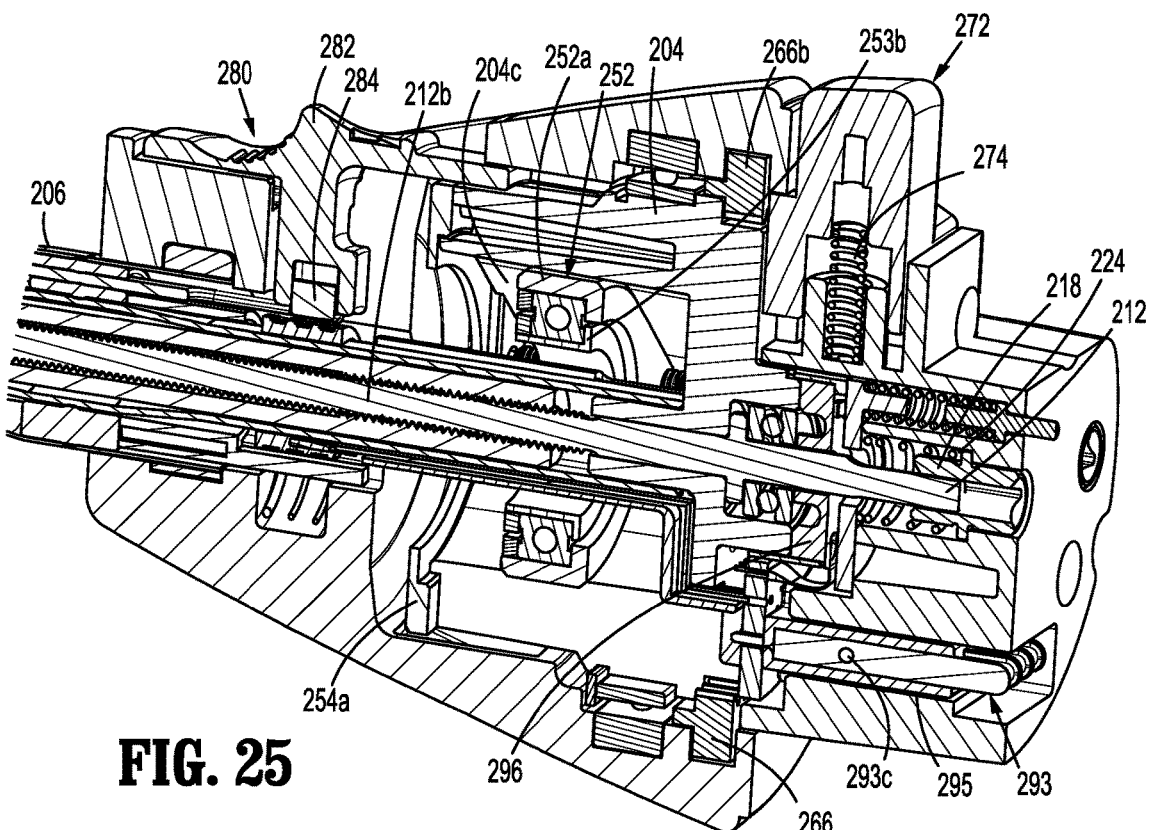
FIG. 25 is an enlarged view of the indicated area of detail of FIG. 24.
Figure 26:
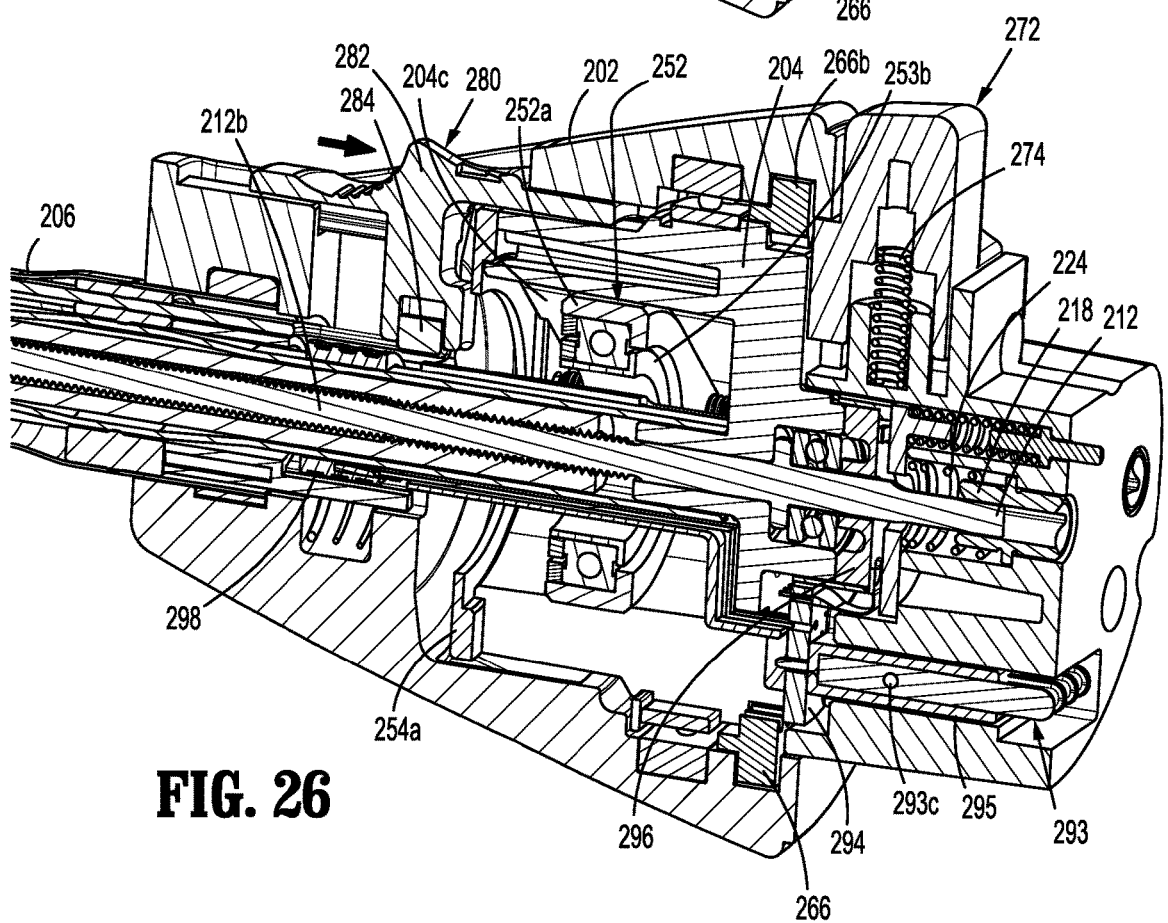
FIG. 26 is an enlarged view of the indicated area of detail of FIG. 24, illustrating a lock button being actuated in a proximal direction.
Figure 27:
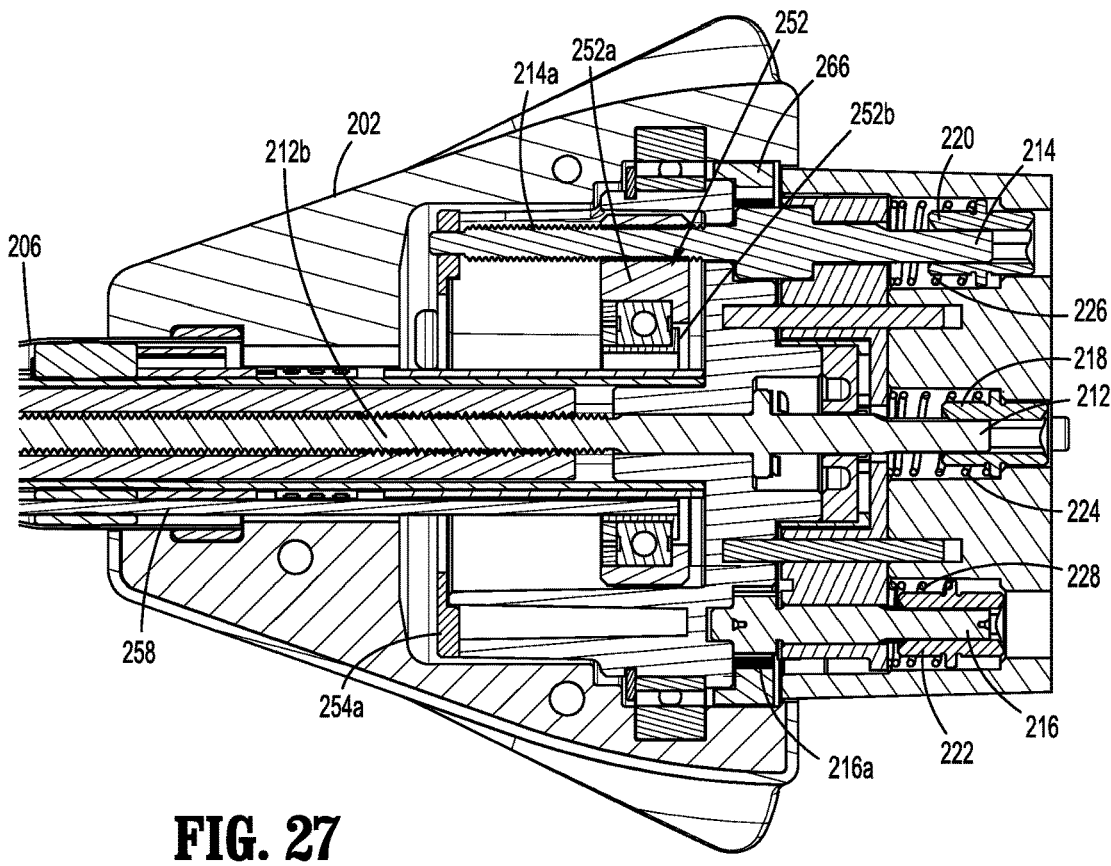
FIG. 27 is a cross-sectional view as taken along section line 27-27 of FIG. 2B.
Figure 28:
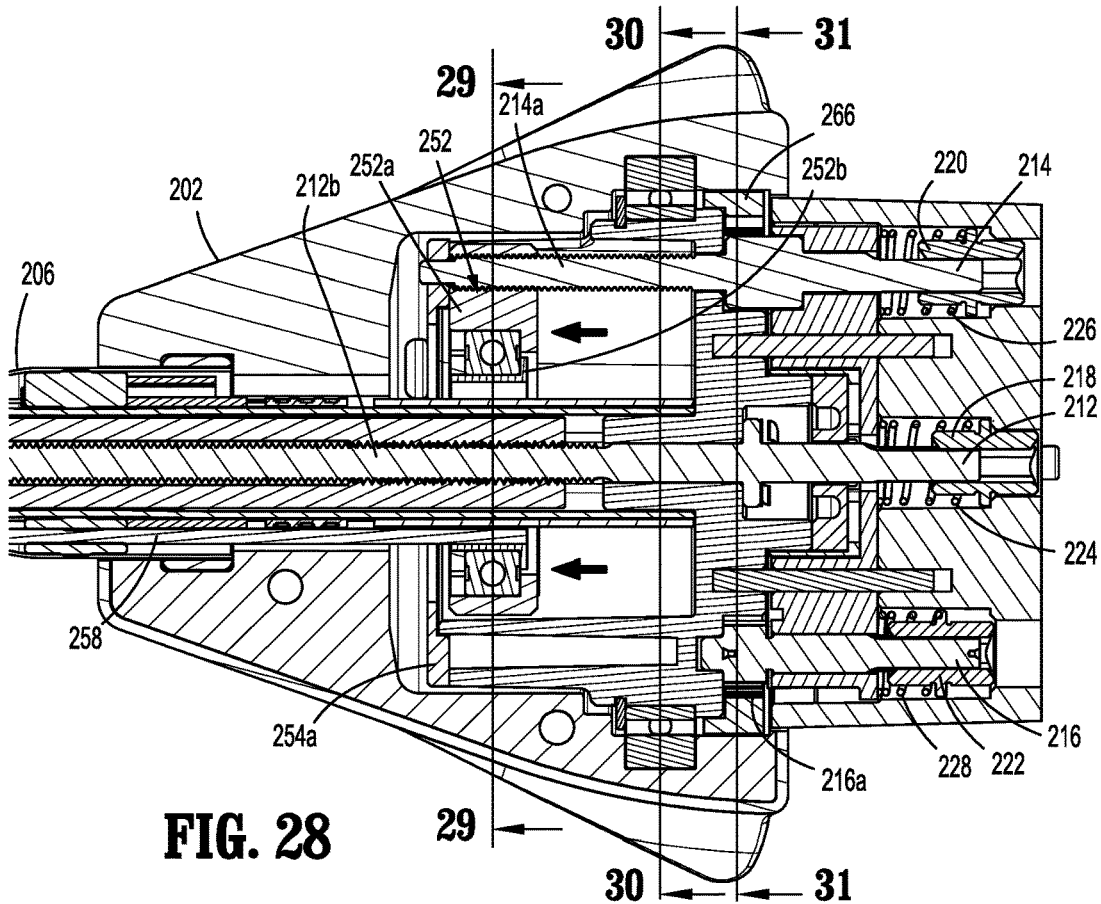
FIG. 28 is a cross-sectional view as taken along section line 27-27 of FIG. 2B, illustrating actuation of the articulation assembly in a distal direction.
Figure 31:
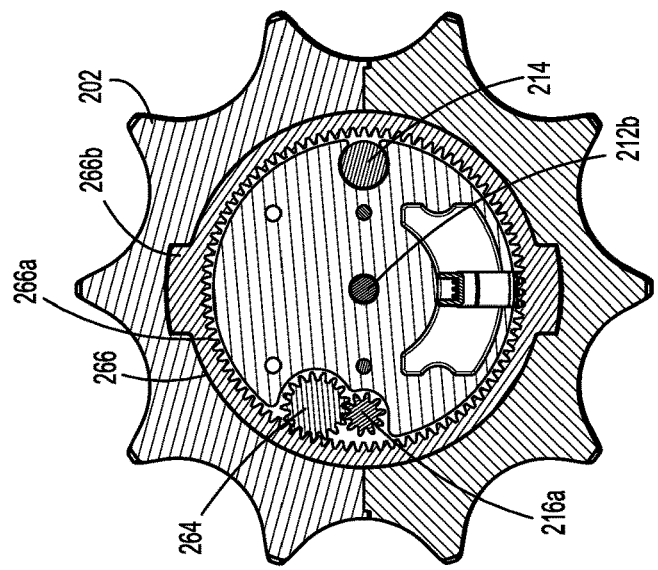
FIG. 31 is a cross-sectional view as taken along section line 31-31 of FIG. 28.
Figure 30:
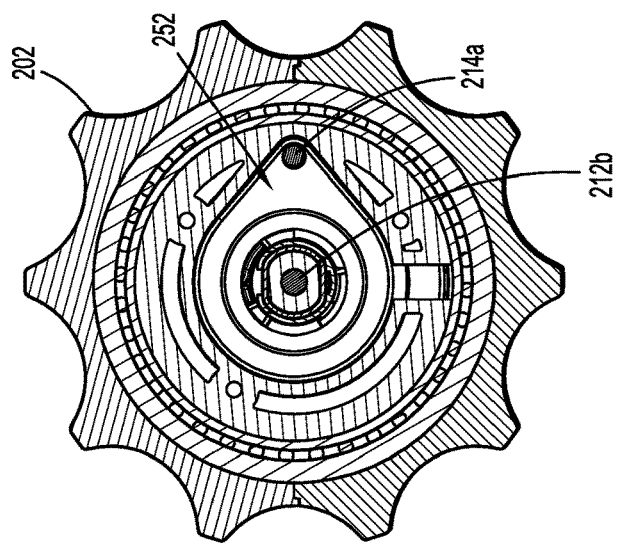
FIG. 30 is a cross-sectional view as taken along section line 30-30 of FIG. 28.
Figure 29:
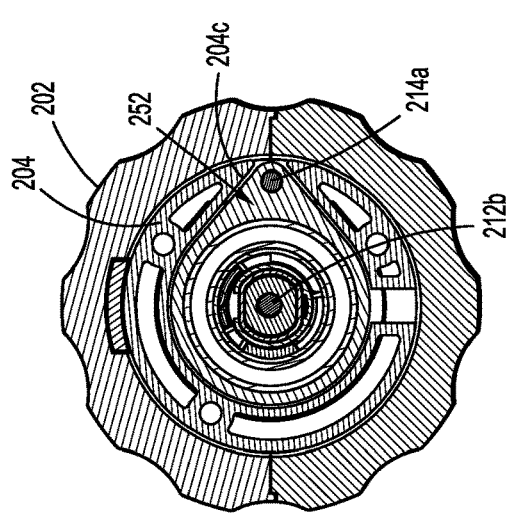
FIG. 29 is a cross-sectional view as taken along section line 29-29 of FIG. 28.
Figure 32:
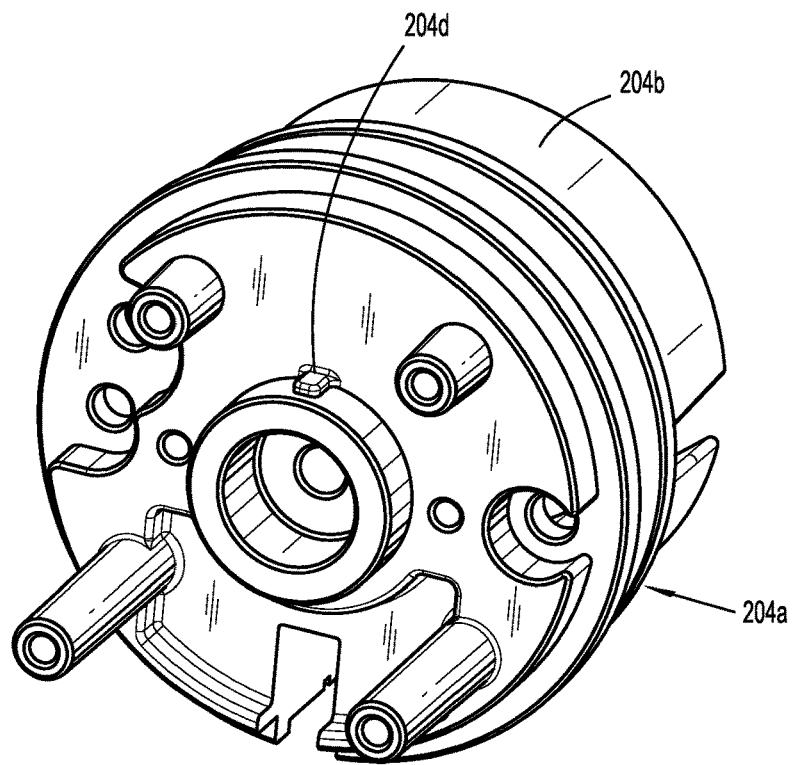
FIG. 32 is a rear, perspective view of a proximal inner housing hub according to the present disclosure.
Figure 33:
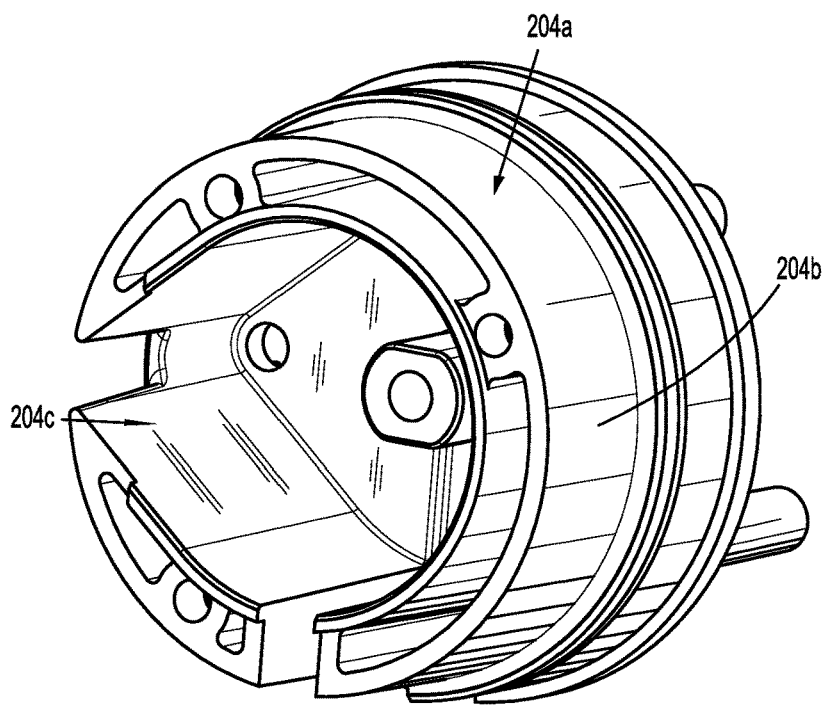
FIG. 33 is a front, perspective view of the proximal inner housing hub of FIG. 32.
Figure 34:
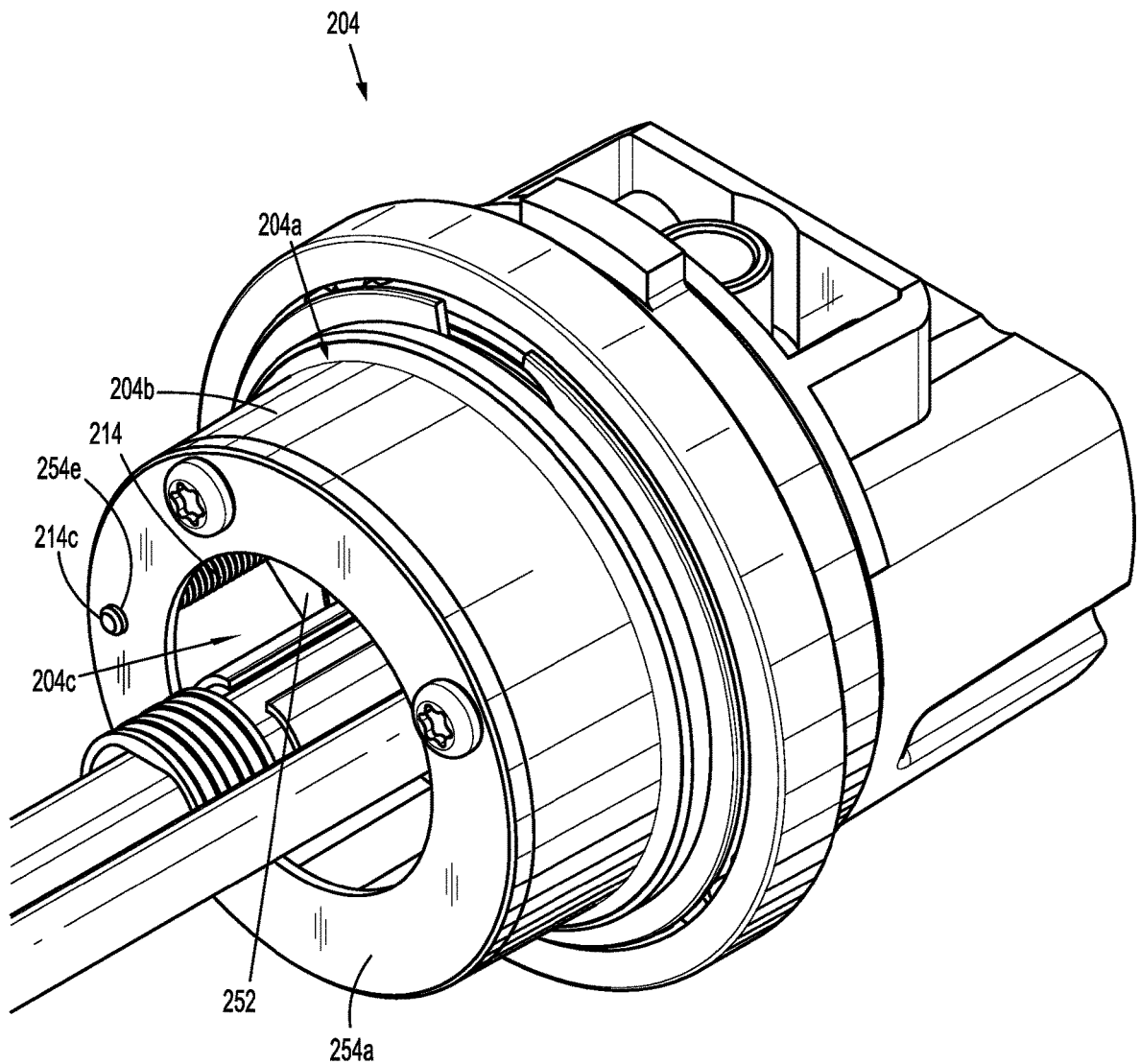
FIG. 34 is a front, perspective view of the proximal inner housing hub of FIGS. 32 and 33 illustrating a first and a second force/rotation transmitting/converting assembly and a reinforcing assembly associated therewith.
Figure 35:
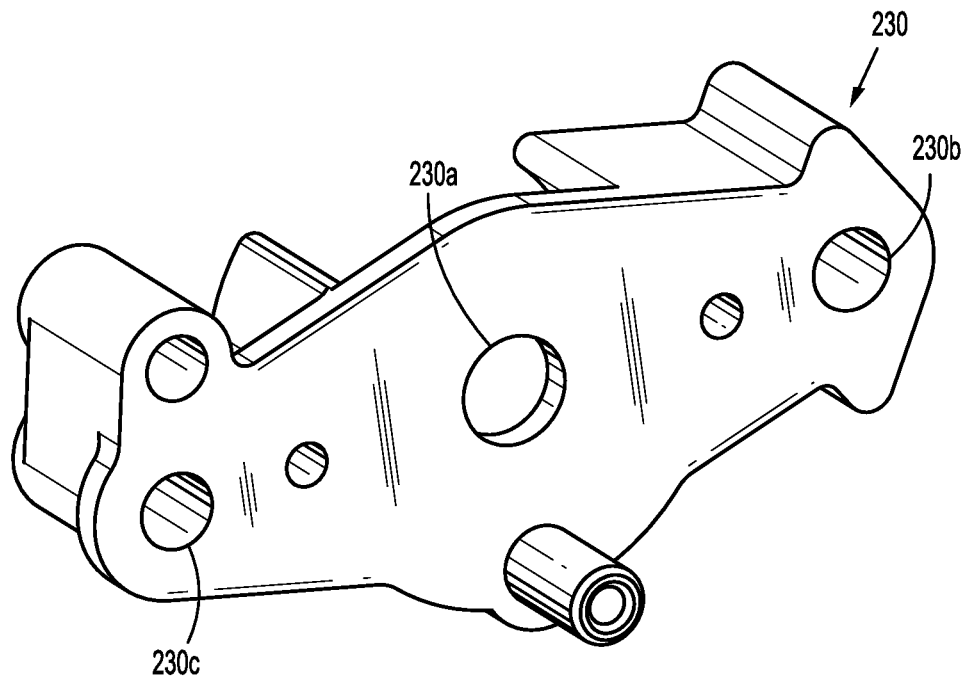
FIG. 35 is a front, perspective view of a plate bushing of the proximal inner housing assembly of the present disclosure.
Figure 36:
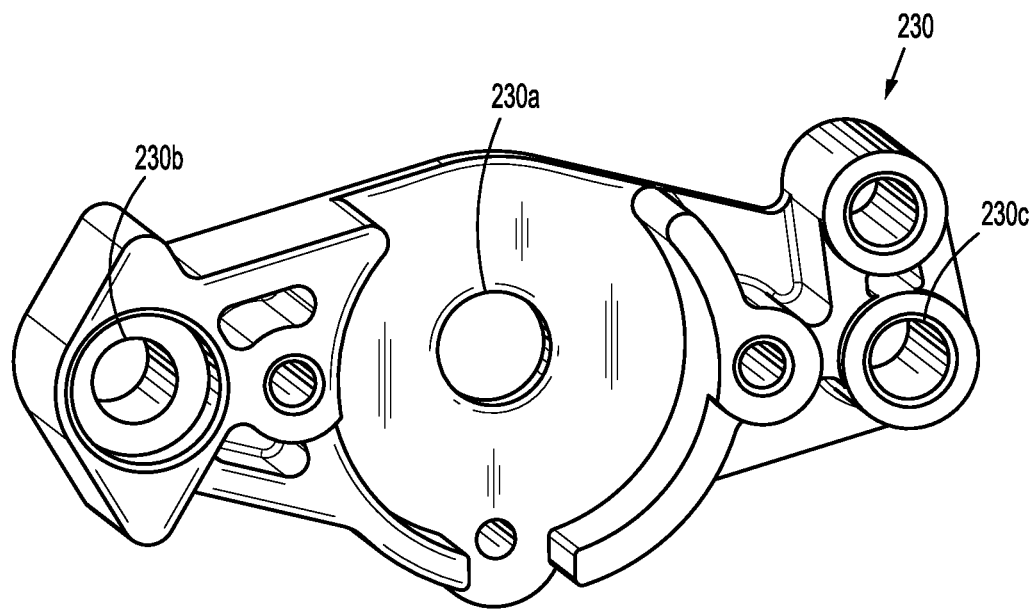
FIG. 36 is a rear, perspective view of the plate bushing of FIG. 35.
Figure 37:
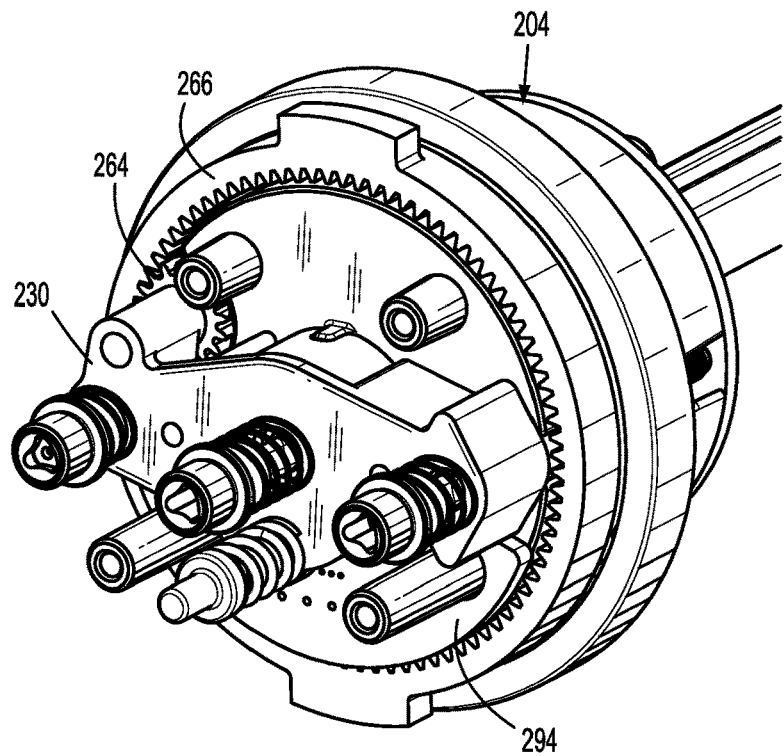
FIG. 37 is a rear, perspective view of the proximal inner housing assembly illustrating the plate bushing of FIGS. 35 and 36 attached thereto.

Specifically, as illustrated in FIG. 6, adapter assembly 200 includes a first, a second and a third force/rotation transmitting/converting assembly 240, 250, 260, respectively, disposed within inner housing 208 and outer tube 206. Each force/rotation transmitting/converting assembly 240, 250, 260 is configured and adapted to transmit or convert a rotation of a first, second and third drive connector 118, 120, 122 of surgical device 100 into axial translation of articulation bar 258 of adapter assembly 200, to effectuate articulation of loading unit 300; a rotation of a ring gear 266 of adapter assembly 200, to effectuate rotation of adapter assembly 200; or axial translation of a distal drive member 248 of adapter assembly 200 to effectuate closing, opening and firing of loading unit 300.

As shown in FIGS. 5, 6 and 24-31, first force/rotation transmitting/converting assembly 240 includes first rotatable proximal drive shaft 212, which, as described above, is rotatably supported within inner housing assembly 204. First rotatable proximal drive shaft 212 includes a non-circular or shaped proximal end portion configured for connection with first connector 218 which is connected to respective first connector 118 of surgical device 100. First rotatable proximal drive shaft 212 includes a distal end portion 212*b* having a threaded outer profile or surface.

First force/rotation transmitting/converting assembly 240 further includes a drive coupling nut 244 rotatably coupled to threaded distal end portion 212*b* of first rotatable proximal drive shaft 212, and which is slidably disposed within outer tube 206. Drive coupling nut 244 is slidably keyed within proximal core tube portion of outer tube 206 so as to be prevented from rotation as first rotatable proximal drive shaft 212 is rotated. In this manner, as first rotatable proximal drive shaft 212 is rotated, drive coupling nut 244 is translated along threaded distal end portion 212*b* of first rotatable proximal drive shaft 212 and, in turn, through and/or along outer tube 206.

First force/rotation transmitting/converting assembly 240 further includes a distal drive member 248 that is mechanically engaged with drive coupling nut 244, such that axial movement of drive coupling nut 244 results in a corresponding amount of axial movement of distal drive member 248. The distal end portion of distal drive member 248 supports a connection member 247 configured and dimensioned for selective engagement with a drive member 374 of drive assembly 360 of loading unit 300 (FIG. 48). Drive coupling nut 244 and/or distal drive member 248 function as a force transmitting member to components of loading unit 300, as described in greater detail below.

In operation, as first rotatable proximal drive shaft 212 is rotated, due to a rotation of first connector sleeve 218, as a result of the rotation of the first respective drive connector 118 of surgical device 100, drive coupling nut 244 is caused to be translated axially along first distal drive shaft 242. As drive coupling nut 244 is caused to be translated axially along first distal drive shaft 242, distal drive member 248 is caused to be translated axially relative to outer tube 206. As distal drive member 248 is translated axially, with connection member 247 connected thereto and engaged with drive member 374 of drive assembly 360 of loading unit 300 (FIG. 48), distal drive member 248 causes concomitant axial translation of drive member 374 of loading unit 300 to effectuate a closure of tool assembly 304 and a firing of tool assembly 304 of loading unit 300.

With reference to FIGS. 5-11, 19 and 23-31, second drive converter assembly 250 of adapter assembly 200 includes second proximal drive shaft 214 rotatably supported within inner housing assembly 204. Second rotatable proximal drive shaft 214 includes a non-circular or shaped proximal end portion configured for connection with second connector or coupler 220 which is connected to respective second connector 120 of surgical device 100. Second rotatable proximal drive shaft 214 further includes a distal end portion 214*b* having a threaded outer profile or surface.

Distal end portion 214*b* of proximal drive shaft 214 is threadably engaged with an articulation bearing housing 252*a* of an articulation bearing assembly 252. Articulation bearing assembly 252 includes a housing 252*a* supporting an articulation bearing 253 having an inner race 253*b* that is independently rotatable relative to an outer race 253*a*. Articulation bearing housing 252*a* has a non-circular outer profile, for example tear-dropped shaped, that is slidably and non-rotatably disposed within a complementary bore 204*c* (FIGS. 25, 26, 29 and 33) of inner housing hub 204*a*.

Second drive converter assembly 250 of adapter assembly 200 further includes an articulation bar 258 having a proximal portion 258*a* secured to inner race 253*b* of articulation bearing 253. A distal portion 258*b* of articulation bar 258 includes a slot 258*c* therein, which is configured to accept a portion 366, e.g., a flag, articulation link (FIG. 48) of loading unit 300. Articulation bar 258 functions as a force transmitting member to components of loading unit 300, as described in greater detail below.

With further regard to articulation bearing assembly 252, articulation bearing assembly 252 is both rotatable and longitudinally translatable. Additionally, it is envisioned that articulation bearing assembly 252 allows for free, unimpeded rotational movement of loading unit 300 when its jaw members 306, 308 are in an approximated position and/or when jaw members 306, 308 are articulated (FIG. 48).

In operation, as second proximal drive shaft 214 is rotated due to a rotation of second connector sleeve 220, as a result of the rotation of the second drive connector 120 of surgical device 100, articulation bearing assembly 252 is caused to be translated axially along threaded distal end portion 214*b* of second proximal drive shaft 214, which in turn causes articulation bar 258 to be axially translated relative to outer tube 206. As articulation bar 258 is translated axially, articulation bar 258, being coupled to articulation link 366 of loading unit 300, causes concomitant axial translation of articulation link 366 of loading unit 300 to effectuate an articulation of tool assembly 304 (FIG. 48). Articulation bar 258 is secured to inner race 253*b* of articulation bearing 253 and is thus free to rotate about the longitudinal axis X-X relative to outer race 253*a* of articulation bearing 253.

As illustrated in FIGS. 6, 17, 18, 20-23, 25-28, 31 and 37-40 and as mentioned above, adapter assembly 200 includes a third force/rotation transmitting/converting assembly 260 supported in inner housing assembly 204. Third force/rotation transmitting/converting assembly 260 includes a rotation ring gear 266 fixedly supported in and connected to outer knob housing 202. Ring gear 266 defines an internal array of gear teeth 266*a* (FIG. 6). Ring gear 266 includes a pair of diametrically opposed, radially extending protrusions 266*b* (FIG. 6) projecting from an outer edge thereof. Protrusions 266*b* are disposed within recesses defined in outer knob housing 202, such that rotation of ring gear 266 results in rotation of outer knob housing 202, and vice a versa.

Third force/rotation transmitting/converting assembly 260 further includes third rotatable proximal drive shaft 216 which, as described above, is rotatably supported within inner housing assembly 204. Third rotatable proximal drive shaft 216 includes a non-circular or shaped proximal end portion configured for connection with third connector 222 which is connected to respective third connector 122 of surgical device 100. Third rotatable proximal drive shaft 216 includes a spur gear 216a keyed to a distal end thereof. A reversing spur gear 264 inter-engages spur gear 216a of third rotatable proximal drive shaft 216 to gear teeth 266a of ring gear 266.

In operation, as third rotatable proximal drive shaft 216 is rotated, due to a rotation of third connector sleeve 222, as a result of the rotation of the third drive connector 122 of surgical device 100, spur gear 216a of third rotatable proximal drive shaft 216 engages reversing gear 264 causing reversing gear 264 to rotate. As reversing gear 264 rotates, ring gear 266 also rotates thereby causing outer knob housing 202 to rotate. As outer knob housing 202 is rotated, outer tube 206 is caused to be rotated about longitudinal axis "X" of adapter assembly 200. As outer tube 206 is rotated, loading unit 300, that is connected to a distal end portion of adapter assembly 200, is also caused to be rotated about a longitudinal axis of adapter assembly 200.

Adapter assembly 200 further includes, as seen in FIGS. 1B, 3-5, 16, 17, 20 and 24-26, an attachment/detachment button 272 supported thereon. Specifically, button 272 is supported on drive coupling assembly 210 of adapter assembly 200 and is biased by a biasing member 274 to an un-actuated condition. Button 272 includes lip or ledge 272a formed therewith that is configured to snap behind a corresponding lip or ledge 108b defined along recess 108a of connecting portion 108 of surgical device 100. In use, when adapter assembly 200 is connected to surgical device 100, lip 272a of button 272 is disposed behind lip 108b of connecting portion 108 of surgical device 100 to secure and retain adapter assembly 200 and surgical device 100 with one another. In order to permit disconnection of adapter assembly 200 and surgical device 100 from one another, button 272 is depresses or actuated, against the bias of biasing member 274, to disengage lip 272a of button 272 and lip 108b of connecting portion 108 of surgical device 100.

With reference to FIGS. 1A, 2A, 2B, 3-5 and 24-26, adapter assembly 200 further includes a lock mechanism 280 for fixing the axial position and radial orientation of distal drive member 248. Lock mechanism 280 includes a button 282 slidably supported on outer knob housing 202. Lock button 282 is connected to an actuation bar 284 that extends longitudinally through outer tube 206. Actuation bar 284 moves upon a movement of lock button 282. Upon a predetermined amount of movement of lock button 282, a distal end of actuation bar 284 may move into contact with a lock out (not shown), which causes the lock out to cam a camming member 288 (FIG. 24) from a recess 249 in distal drive member 248. When camming member 288 is in engagement with recess 249 (e.g., at least partially within recess 249, see FIGS. 6 and 24), the engagement between camming member 288 and distal drive member 248 effectively locks the axial and rotational position of end effector 300 that is engaged with connection member 247.

In operation, in order to lock the position and/or orientation of distal drive member 248, a user moves lock button 282 from a distal position to a proximal position (FIGS. 25 and 26), thereby causing the lock out (not shown) to move proximally such that a distal face of the lock out moves out of contact with camming member 288, which causes camming member 288 to cam into recess 249 of distal drive member 248. In this manner, distal drive member 248 is prevented from distal and/or proximal movement. When lock button 282 is moved from the proximal position to the distal position, the distal end of actuation bar 284 moves distally into the lock out, against the bias of a biasing member (not shown), to force camming member 288 out of recess 249, thereby allowing unimpeded axial translation and radial movement of distal drive member 248.

Reference may be made to U.S. Pat. No. 9,597,104, the entire content of which is incorporated herein by reference, for a more detailed discussion of the construction and operation of lock mechanism 280.

With reference to FIGS. 1B, 6, 12A-15 and 25-28, adapter assembly 200 includes an electrical assembly 290 supported on and in outer knob housing 202 and inner housing assembly 204. Electrical assembly 290 includes an electrical connector 292 supported on a circuit board 294, for electrical connection to a corresponding electrical plug 190 disposed in connecting portion 108 of surgical device 100.

With particular reference to FIGS. 12A-12D, electrical connector 292 includes a plurality of electrical contact pins 293 and a housing or connector housing 295. Electrical contact pins 293 serve to allow for calibration and communication of life-cycle information to the circuit board of surgical device 100 via electrical plugs 190 that are electrically connected to the circuit board (not shown) of surgical device 100.

Each electrical contact pin 293 includes a distal portion 293a and a proximal portion 293b. Distal portion 293a of each contact pin 293 is configured to engage circuit board 294, e.g., via soldering. Proximal portion 293b of each contact pin 293 is configured to releasably engage corresponding electrical plug 190 disposed in connecting portion 108 of surgical device 100. With continued reference to FIGS. 12A-12D, distal portion 293a of each electrical contact pin 293 is tapered to facilitate insertion into holes 294a (FIG. 12B) of circuit board 294. Proximal portion 293b of each electrical contact pin 293 includes a rectangular cross-section, and is tapered and chamfered to facilitate engagement and disengagement with electrical plug 190.

Additionally, each electrical contact pin 293 includes a hole 293c extending laterally therethrough. Hole 293c is configured to facilitate the connection between electrical contact pins 293 and housing 295. It is envisioned that housing 295 is over-molded, such that portions of the over-mold extend through holes 293c in electrical contact pins 293. As can be appreciated, the engagement between electrical contact pins 293 and housing 295 helps maintain proper alignment of pins 293 to further facilitate engagement between electrical connector 292 and circuit board 294 and electrical plug 190, and to further facilitate engagement between electrical connector 292 and electrical plug 190. While seven electrical contact pins 293 are shown, it is envisioned that more or fewer electrical contact pins 293 are included with electrical assembly 290.

With continued reference to FIGS. 12A-12D, housing 295 of electrical connector 292 includes a rectangular cross-section. The rectangular cross-section of housing 295 is configured to mate with a rectangular opening of proximal cap 210a (FIGS. 5 and 6) of drive coupling assembly 210 to prevent radial movement therebetween.

Housing 295 also includes a plurality of projections 297 extending therefrom. Projections 297 each include a distal face 297a and a proximal face 297b. Distal face 297a of each projection 297 is configured and positioned to contact circuit board 294 during insertion of electrical connector 292. Thus, distal face 297a of each projection 297 prevents electrical contact pins 293 of electrical connector 292 from being inserted too far distally into holes 294a of circuit board 294. While distal face 297a of each projection 297 is illustrated as being flush with a distal face 295a of housing 295 (FIG. 12D), it is envisioned that distal face 297a of each projection 297 is positioned farther proximally or distally than distal face 295a of housing 295. Proximal face 297b of each projection 297 is configured and positioned to prevent disengagement between electrical connector 292 and circuit board 294, e.g., during disengagement between surgical device 100 and adapter assembly 200. More particularly, a surface of proximal cap 210 of electrical assembly 290 is configured to abut proximal face 297b of at least one or all projections 297, thus preventing proximal movement of electrical connector 292 with respect to circuit board 294. In the illustrated embodiment, two projections 297 extend from a first surface 295b of housing 295, and two projections 297 extend from a second surface 295c of housing 295. However, housing 295 may include more or fewer projections 297.

Electrical assembly 290 further includes a strain gauge 296 electrically connected to circuit board 294. Strain gauge 296 is provided with a notch 296a which is configured and adapted to receive stem 204d of hub 204a of inner housing assembly 204. Stem 204d of hub 204a functions to restrict rotational movement of strain gauge 296. As illustrated in FIGS. 25-28, first rotatable proximal drive shaft 212 extends through strain gauge 296. Strain gauge 296 provides a closed-loop feedback to a firing/clamping load exhibited by first rotatable proximal drive shaft 212.

Electrical assembly 290 also includes a slip ring 298 disposed within outer tube 206. Slip ring 298 is in electrical connection with circuit board 294. Slip ring 298 functions to permit rotation of first rotatable proximal drive shaft 212 and axial translation of drive coupling nut 244 while still maintaining electrical contact of electrical contact rings 298a thereof with at least another electrical component within adapter assembly 200, and while permitting the other electrical components to rotate about first rotatable proximal drive shaft 212 and drive coupling nut 244

Electrical assembly 290 may include a slip ring cannula or sleeve 299 positioned core tube of tube 206 to protect and/or shield any wires extending from slip ring 298.

Turning now to FIGS. 6, 11, 14, 32 and 33, inner housing assembly 204 has been designed to reduce incidents of racking of second proximal drive shaft 214 as drive shaft 214 rotates to axially translate articulation bearing assembly 252. Inner housing assembly 204 includes a hub 204a having a distally oriented annular wall 204b defining a substantially circular outer profile, and defining a substantially tear-drop shaped inner recess or bore 204c. Bore 204c of hub 204a is shaped and dimensioned to slidably receive articulation bearing assembly 252 therewithin.

Inner housing assembly 204 includes a ring plate 254a (FIG. 34) secured to a distal face of distally oriented annular wall 204b of hub 204a. Plate 254a defines an aperture 254e therethrough that is sized and formed therein so as to be aligned with second proximal drive shaft 214 and to rotatably receive a distal tip 214c of second proximal drive shaft 214. In this manner, distal tip 214c of second proximal drive shaft 214 is supported and prevented from moving radially away from a longitudinal rotational axis of second proximal drive shaft 214 as second proximal drive shaft 214 is rotated to axially translate articulation bearing assembly 252.

As illustrated in FIGS. 14, 32, 39 and 40, hub 204a defines a feature (e.g., a stem or the like) 204d projecting therefrom which functions to engage notch 296a of strain gauge 296 of electrical assembly 290 to measure forces experienced by shaft 212 as surgical device 100 is operated.

With reference to FIGS. 35-40, a plate bushing 230 of inner housing assembly 204 is shown and described. Plate bushing 230 extends across hub 204a of inner housing assembly 204 and is secured to hub 204a by fastening members. Plate bushing 230 defines three apertures 230a, 230b, 230c that are aligned with and rotatably receive respective first, second and third proximal drive shafts 212, 214, 216 therein. Plate bushing 230 provides a surface against which first, second and third biasing members 224, 226 and 228 come into contact or rest against.

Figure 40:
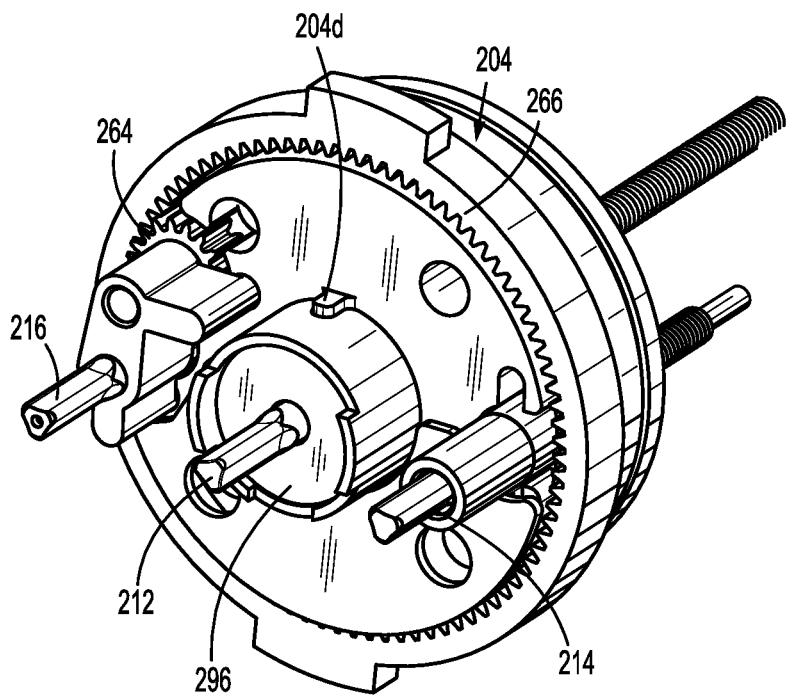
FIG. 40 is a rear, perspective view of the proximal inner housing assembly of FIG. 37 with connector sleeves removed therefrom.
Figure 41:
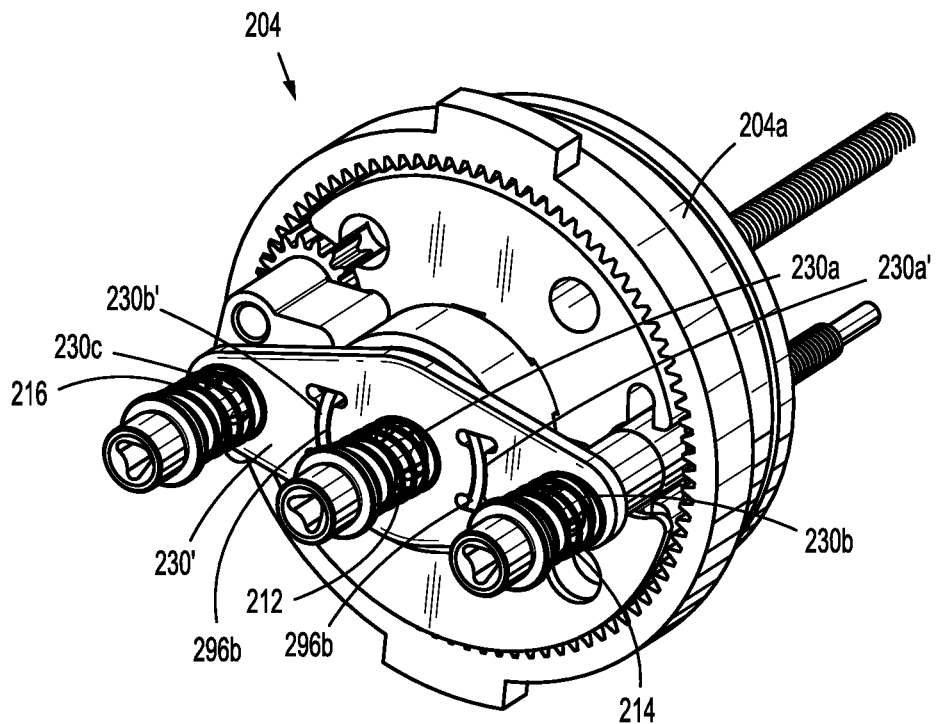
FIG. 41 is a rear, perspective of the inner housing assembly of FIG. 37 illustrating a support plate, according to another embodiment of the present disclosure, coupled thereto.
Figure 42:
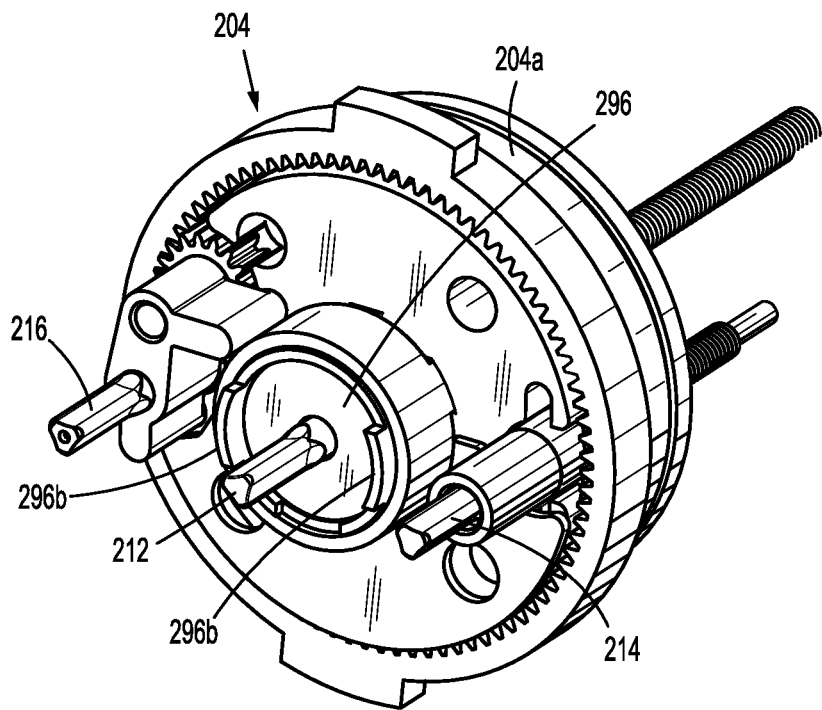
FIG. 42 is a rear, perspective of the inner housing assembly of FIG. 41 with the support plate removed therefrom.
Figure 43:
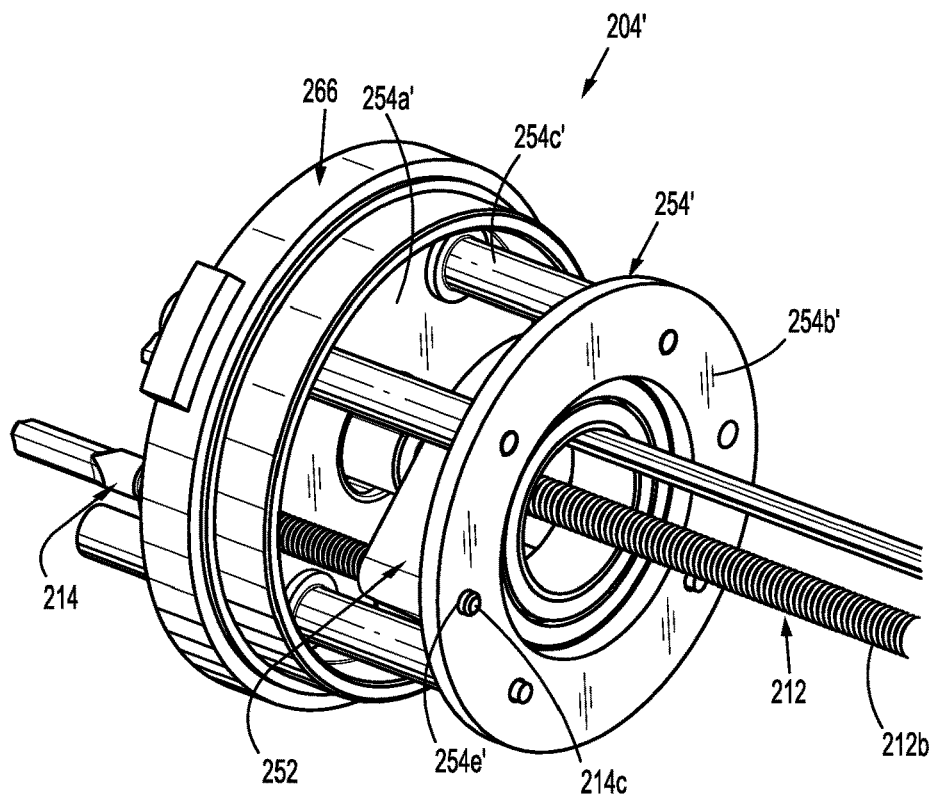
FIG. 43 is a front, perspective view of an inner housing assembly according to another embodiment of the present disclosure with the outer knob housing, the proximal inner housing removed therefrom.
Figure 44:
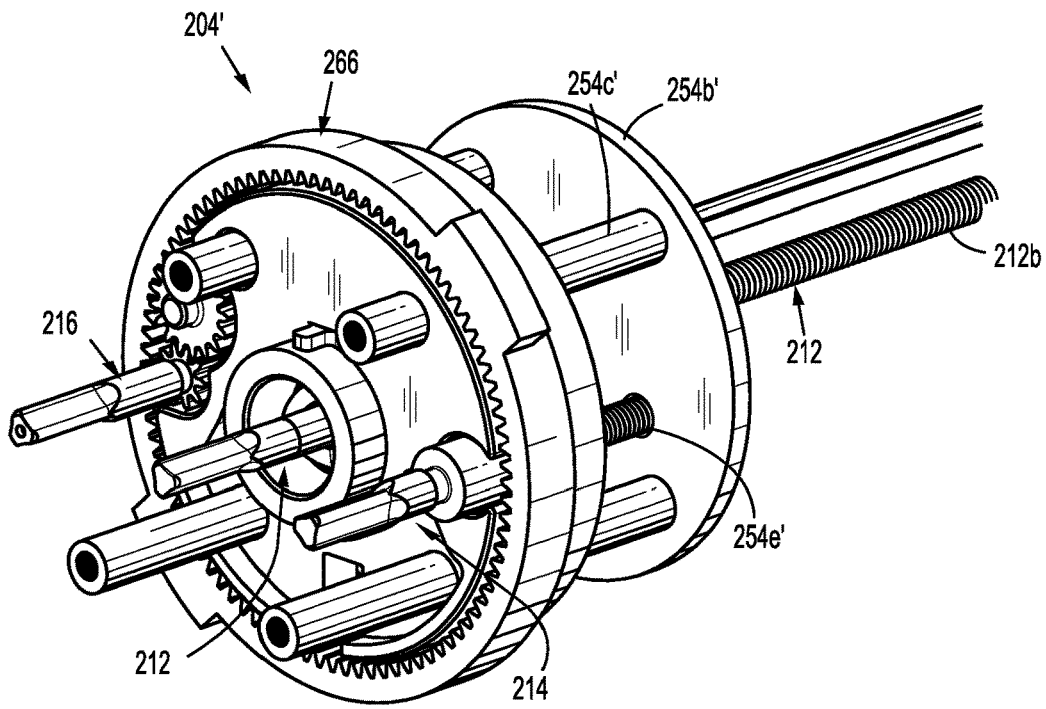
FIG. 44 is a rear, perspective view of the inner housing assembly of FIG. 43 with the outer knob housing, the proximal inner housing and the articulation assembly removed therefrom.

While plate bushing 230 has been shown and described as being a unitary monolithic piece, as illustrated in FIGS. 6 and 37-40, it is envisioned and within the scope of the present application that plate bushing 230 may be separated into several parts including, and not limited to, as seen in FIGS. 40-42, a support plate 230' extending across drive shafts 212, 214, 216, and a separate bushing for each of drive shafts 212, 214, 216 and disposed between the support plate 230' and hub 204a of inner housing assembly 204. Support plate 230' may include a pair of slots 230a', 230b' formed therein, which are configured and adapted to receive tabs 296b of strain gauge 296 that project axially therefrom.

Turning now to FIGS. 43-47, an inner housing assembly 204' according to another embodiment of the present disclosure is shown and will be described. In order to reduce incidents of racking (i.e., distal end 214b of second proximal drive shaft 214 moving radially away from a longitudinal rotational axis thereof) of second proximal drive shaft 214 as drive shaft 214 rotates to axially translate articulation bearing assembly 252, inner housing assembly 204' may include a reinforcement frame or bracket assembly 254'. Bracket assembly 254' includes a first plate 254a' and a second plate 254b' integrally connected to and spaced a distance from first plate 254a' by a plurality of connecting rods 254c' extending therebetween.

First plate 254a' is disposed adjacent to or in close proximity to ring gear 266 and defines an aperture 254d' therethrough. Aperture 254d' is sized and formed in first plate 254a' so as to be aligned with second proximal drive shaft 214 and to permit second proximal drive shaft 214 to freely rotate therewithin. Second plate 254b' is spaced from first plate 254a' so as to be disposed at a distal free end of second proximal drive shaft 214. Second plate 254b' defines an aperture 254e' therethrough. Aperture 254e' is sized and formed in second plate or flange 254b' so as to be aligned with second proximal drive shaft 214 and to rotatably receive a distal tip 214c of second proximal drive shaft 214.

In this manner, distal tip 214c of second proximal drive shaft 214 is supported and prevented from moving radially away from a longitudinal rotational axis of second proximal drive shaft 214 as second proximal drive shaft 214 is rotated to axially translate articulation bearing assembly 252.

Figure 38:
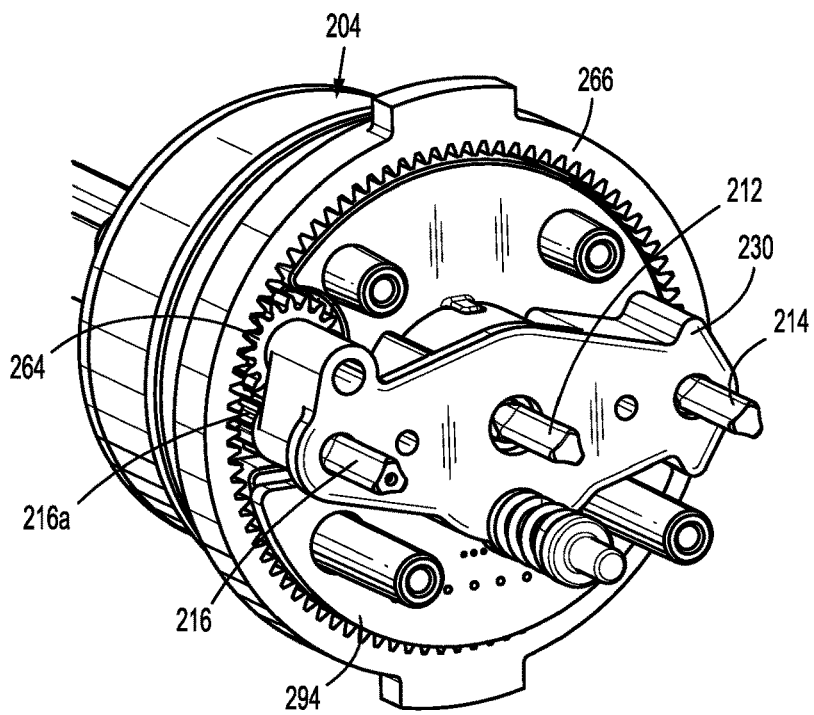
FIG. 38 is a rear, perspective view of the proximal inner housing assembly of FIG. 37 with connector sleeves removed therefrom.
Figure 39:
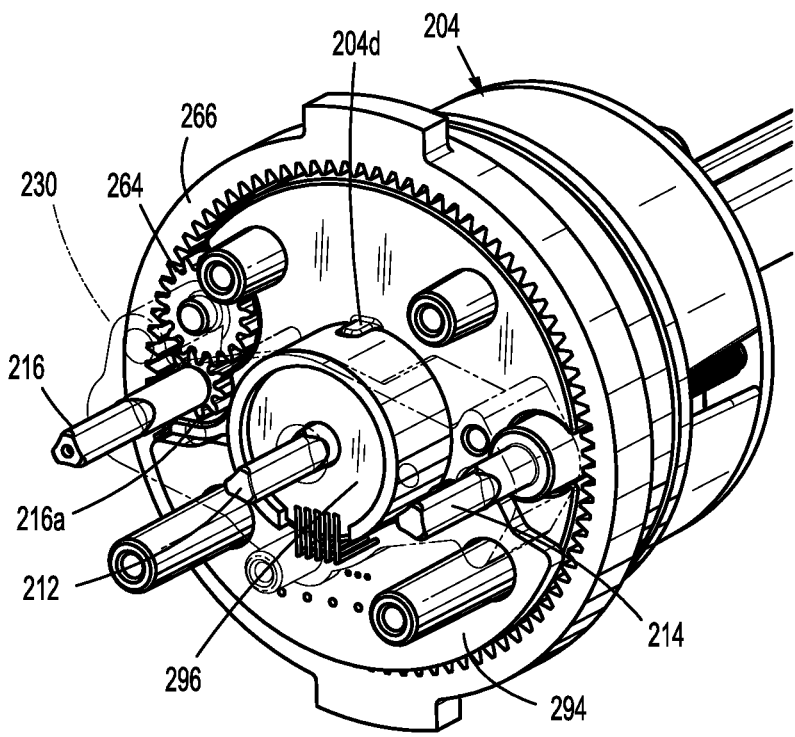
FIG. 39 is a rear, perspective view of the proximal inner housing assembly of FIG. 37 with connector sleeves removed therefrom and the plate bushing shown in phantom.

As illustrated in FIGS. 38, 46 and 47, inner housing assembly 204' may include a reinforcing sleeve 255' disposed about bracket assembly 254' to further reinforce bracket assembly 254'. It is contemplated in an embodiment that reinforcing sleeve 255' may be interposed between first plate 254a' and second plate 254b' of bracket assembly 254'. It is further contemplated that reinforcing sleeve 255' may be interposed between second plate 254b' and a distally oriented face of proximal inner housing assembly 204'.

In accordance with the present disclosure, an overall length of adapter assembly 200 has been reduced as compared to prior adapter assemblies that have been developed to transmit/convert forces/rotations from surgical device 100 to loading unit 300. By reducing an overall length of adapter assembly 200, a center of gravity of an assembled surgical device 100, adapter assembly 200 and loading unit 300 has been shifted proximally as compared to a center of gravity of an assembled surgical device 100, a prior adapter assembly and a loading unit 300. As such, a level of comfort to the end user in using the electromechanical surgical system of the present disclosure has been increased, and a level of fatigue has been decreased.

In operation, when a button of surgical device 100 is activated by the user, the software checks predefined conditions. If conditions are met, the software controls the motors and delivers mechanical drive to the attached surgical stapler, which can then open, close, rotate, articulate or fire depending on the function of the pressed button. The software also provides feedback to the user by turning colored lights on or off in a defined manner to indicate the status of surgical device 100, adapter assembly 200 and/or loading unit 300.

Reference may be made to U.S. Pat. No. 7,819,896, entitled "TOOL ASSEMBLY FOR A SURGICAL STAPLING DEVICE" for a detailed discussion of the construction and operation of loading unit 300, as illustrated in FIGS. 1 and 48.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An adapter assembly for selectively interconnecting a surgical loading unit and a surgical device, the adapter assembly comprising:
   an electrical assembly including a strain gauge and a circuit board, the strain gauge is:
   electrically connected to the circuit board; and
   configured to selectively electrically connect to a complementary electrical element of the surgical device.

2. The adapter assembly according to claim 1, wherein the electrical assembly includes at least one contact pin configured to selectively electrically connect to the complementary electrical element of the surgical device.

3. The adapter assembly according to claim 2, wherein the electrical assembly includes a connector housing, wherein the at least one contact pin of the electrical assembly extends through the connector housing of the electrical assembly.

4. The adapter assembly according to claim 3, wherein the at least one contact pin of the electrical assembly extends entirely through the connector housing of the electrical assembly.

5. The adapter assembly according to claim 3, wherein the at least one contact pin of the electrical assembly is fixed to the connector housing of the electrical assembly.

6. The adapter assembly according to claim 3, wherein the connector housing of the electrical assembly is secured to the at least one contact pin of the electrical assembly via over-molding.

7. The adapter assembly according to claim 6, wherein the at least one contact pin of the electrical assembly includes a hole extending therethrough, and wherein a portion of the connector housing of the electrical assembly extends through the hole of the at least one contact pin.

8. The adapter assembly according to claim 2, wherein a proximal portion of the at least one contact pin of the electrical assembly includes a rectangular cross-section.

9. The adapter assembly according to claim 3, wherein the connector housing of the electrical assembly includes at least one projection extending from a surface thereof.

10. The adapter assembly according to claim 9, wherein a proximal face of the at least one projection of the connector housing of the electrical assembly is configured to abut a surface of a proximal cap.

11. The adapter assembly according to claim 2, further comprising an electrical connector, wherein the at least one contact pin of the electrical assembly is included on the electrical connector.

12. The adapter assembly according to claim 1, wherein the strain gauge is supported on the circuit board.

13. The adapter assembly according to claim 1, wherein the electrical assembly further includes a slip ring in electrical connection with the circuit board, and wherein the slip ring includes an electrical contact for maintaining electrical contact with at least one electrical component of the adapter assembly.

14. The adapter assembly according to claim 1, wherein the connector housing of the electrical assembly includes at least one projection extending from a surface thereof, a distal face of the at least one projection is configured to abut the circuit board when the at least one contact pin of the electrical assembly is electrically connected to the circuit board.

15. An adapter assembly for selectively interconnecting a surgical loading unit and a surgical device, the adapter assembly comprising:
   an electrical assembly including:
   at least one contact pin configured to selectively electrically connect to a complementary electrical element of the surgical device, wherein a proximal portion of the at least one contact pin includes a rectangular cross-section; and
   a circuit board supported in the adapter assembly and supporting the at least one contact pin.

16. The adapter assembly according to claim 15, wherein the electrical assembly includes a strain gauge electrically connected to the circuit board.

17. The adapter assembly according to claim 16, wherein the strain gauge is supported on the circuit board so as to monitor reactive forces acting on the adapter assembly during operation of the surgical device.

* * * * *